(12) United States Patent
Hansen et al.

(10) Patent No.: US 11,981,664 B2
(45) Date of Patent: May 14, 2024

(54) PHOTORESPONSIVE NUTLIN DERIVATIVES AND USES THEREOF

(71) Applicants: Rijksuniversiteit Groningen, Groningen (NL); Stichting Het Nederlands Kanker Instituut-Antoni van Leeuwenhoek Ziekenhuis, Amsterdam (NL)

(72) Inventors: Mickel Jens Hansen, Eext (NL); Bernard Lucas Feringa, Paterswolde (NL); Femke Maria Feringa, Amsterdam (NL)

(73) Assignees: Rijksuniversiteit Groningen, Groningen (NL); Stichting Het Nederlands Kanker Instituut-Antoni van Leeuwenhoek Ziekenhuis, Amsterdam (NL)

( * ) Notice: Subject to any disclaimer, the term of this patent is extended or adjusted under 35 U.S.C. 154(b) by 563 days.

(21) Appl. No.: 17/282,274

(22) PCT Filed: Oct. 2, 2019

(86) PCT No.: PCT/NL2019/050659
§ 371 (c)(1),
(2) Date: Apr. 1, 2021

(87) PCT Pub. No.: WO2020/071911
PCT Pub. Date: Apr. 9, 2020

(65) Prior Publication Data
US 2021/0371406 A1 Dec. 2, 2021

(30) Foreign Application Priority Data
Oct. 3, 2018 (EP) ..................... 18198468

(51) Int. Cl.
*C07D 405/12* (2006.01)
*A61K 41/00* (2020.01)

(52) U.S. Cl.
CPC ........ *C07D 405/12* (2013.01); *A61K 41/0042* (2013.01)

(58) Field of Classification Search
CPC .......................... C07D 405/12; A61K 41/0042
See application file for complete search history.

(56) References Cited

PUBLICATIONS

Klán, Petr, et al., "Photoremovable Protecting Groups in Chemistry and Biology: Reaction Mechanisms and Efficacy," Chemical Reviews, vol. 113, No. 1, pp. 119-191 (2013).

Ding, Qingjie, et al., "Discovery of RG7388, A Potent and Selective p53-MDM2 Inhibitor in Clinical Development," Journal of Medicinal Chemistry, vol. 56, No. 14, pp. 5979-5983 (2013).

Jansen, Mickel J., et al., "Photoactivation of MDM2 Inhibitors: Controlling Protein-Protein Interaction with Light," Journal of the American Chemical Society, vol. 140, No. 41, pp. 13136-13141 (2018).

*Primary Examiner* — Samantha L Shterengarts
*Assistant Examiner* — Karen Cheng
(74) *Attorney, Agent, or Firm* — Hoffmann & Baron LLP

(57) ABSTRACT

The invention relates to the field of medicine and medicinal chemistry, more in particular to the design, manufacture and use of anti-cancer drugs that can be activated by an external stimulus that can be applied in a spatiotemporal fashion. Provided herein is a compound having the chemical structure or a pharmaceutically acceptable salt thereof.

Figure 1B:
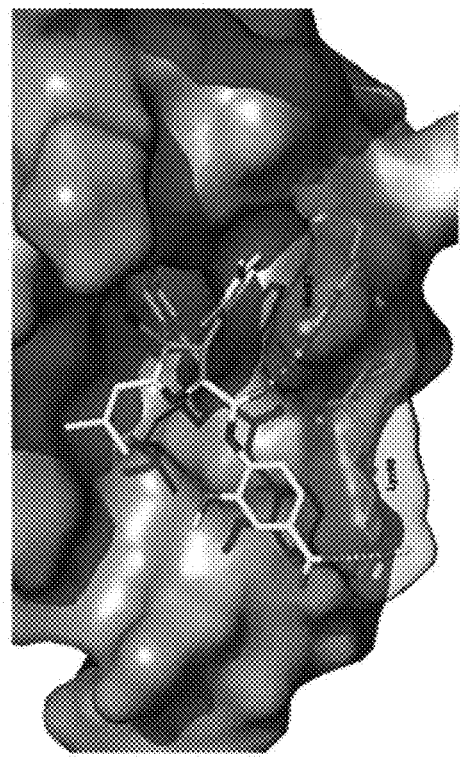
Figure 1A:
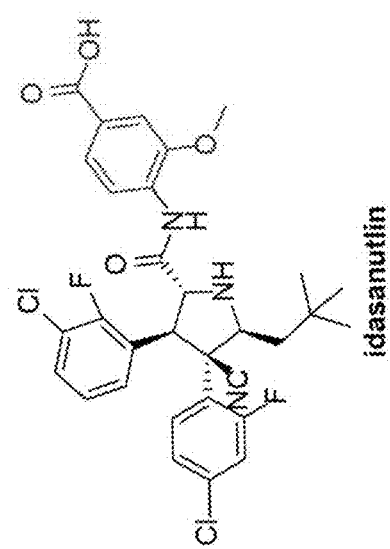
Figure 1C:
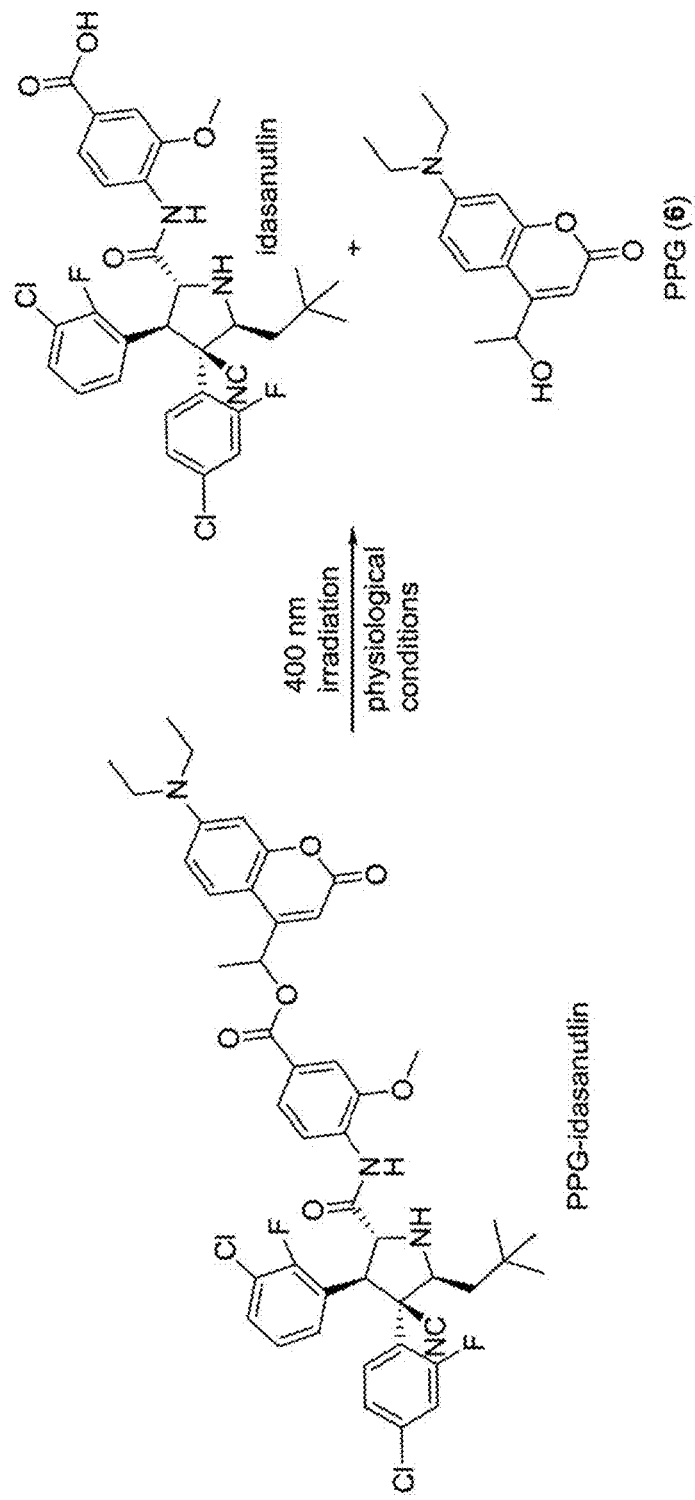
Figure 1E:
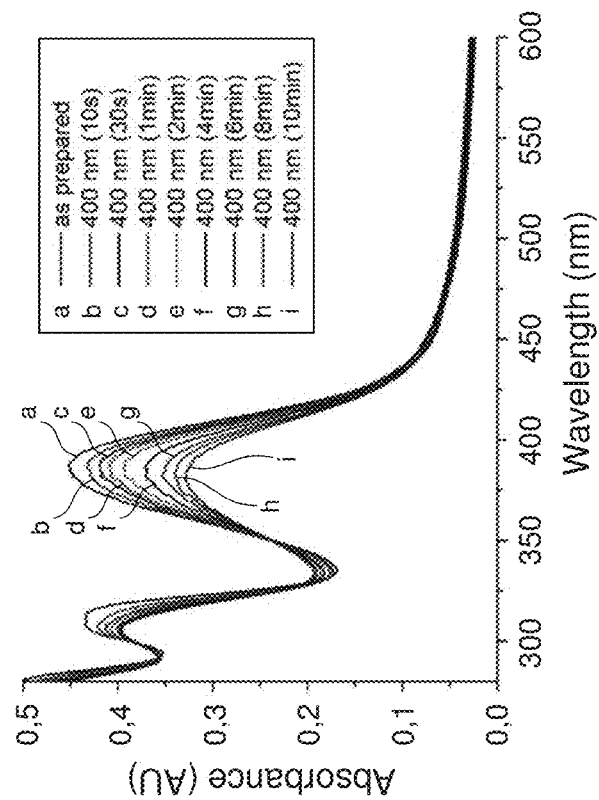
Figure 1D:
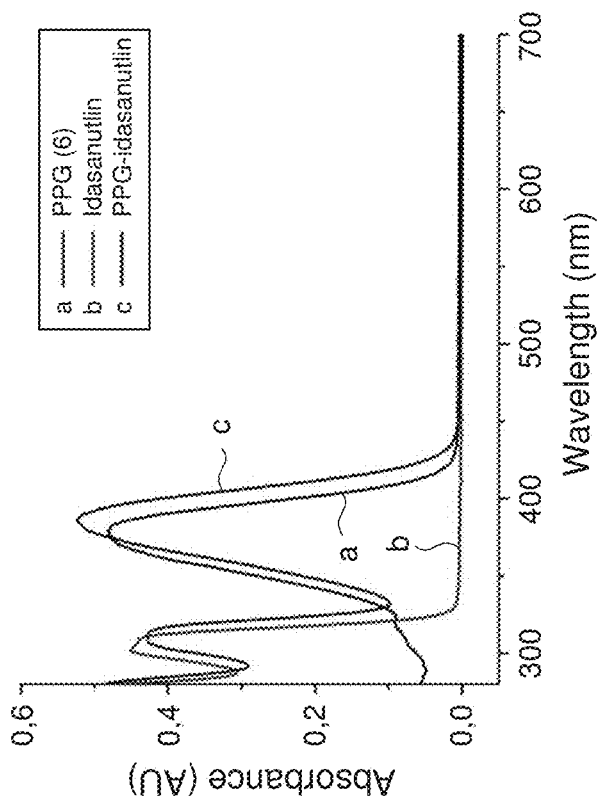

27 Claims, 11 Drawing Sheets a → Example cell not hit by the laser
b → Example cell hit by the laser (0,1 sec pulse per position)

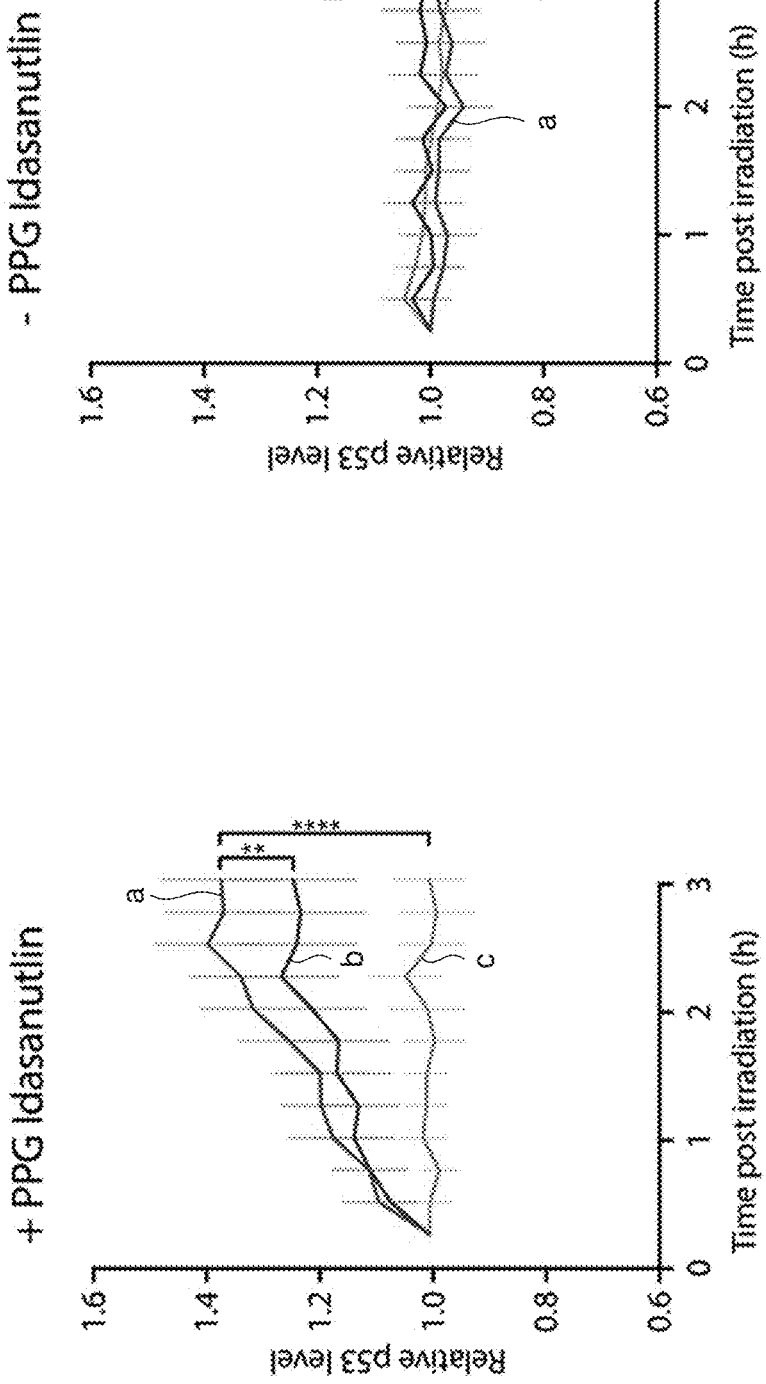

PHOTORESPONSIVE NUTLIN DERIVATIVES AND USES THEREOF

This application is the U.S. National Phase of International Patent Application Number PCT/NL2019/050659 filed Oct. 2, 2019, which claims priority to EP 18198468.3 filed Oct. 3, 2018 each of which is incorporated herein by reference.

The invention relates to the field of medicine and medicinal chemistry. More in particular, it relates to the design, manufacture and use of anti-cancer drugs that can be activated by an external stimulus that can be applied in a spatiotemporal fashion.

Cancer is one of the major causes of death in the developed world. Long-standing drawbacks of cancer chemotherapy are its inherent toxicity and associated adverse effects. To fight these selectivity issues, targeting pathways that are exclusively needed for cancer cell survival have been explored.[1-4] One way of controlling these cellular pathways is by interfering with cancer cell-specific protein-protein interactions (PPIs). Interestingly, by controlling PPIs, remote control of a specific protein can be achieved, which opens up new targeting strategies in anti-cancer treatment.

The best known tumor suppressor protein, p53, is heavily involved in PPIs and plays an important role in cell-cycle control, apoptosis, DNA repair and cellular stress responses.[5,6] Activation of p53 by various types of stress can drive cellular senescence, which is an irreversible cell-cycle arrest, to prevent potential transformation of the damaged cell. Utilizing its role in apoptosis and senescence, reactivation of the p53 signalling pathway remains a preeminent target for cancer treatment.[7,8] A major concern in p53 reactivating therapies is its effect on normal cells, since upregulation of p53 protein expression by itself is sufficient to induce senescence or apoptosis in all cycling cells.[9,10] Therefore, the selective activation of the p53 pathway in cancerous tissue is a key challenge, as it would greatly increase the potential success for therapeutical application.

One of the main repressors of p53 activity is the MDM2-protein. MDM2 interacts with p53 to promote its ubiquitylation, making it a target for degradation by the proteasome.[11-13] The regulatory PPI between p53 and MDM2 makes the latter an interesting target in anti-cancer drug development. Recently, a class of MDM2 inhibitors (nutlins) has been developed allowing the selective activation of the tumor suppressing p53 pathway.[14-16] See also WO2010/031713, WO2012/07409, WO2012/34954 and WO2013/178570. Nutlins bind to the p53-binding site of MDM2, inhibiting proteolytic breakdown of p53, resulting in the stabilization of p53 which arrests rapid cell division and can induce senescence.[9]

Selectivity remains a major challenge in anti-cancer therapy which potentially can be overcome by local activation of a cytotoxic drug. Such triggered activation can be obtained through modification of a drug with a photoprotecting group (PPG), and subsequent irradiation in the chosen place and time.

The present inventors recognized that light activation to regulate protein-protein interactions between MDM2 and p53 offers exciting opportunities to control a multitude of biological processes and has the potential to circumvent common selectivity issues in anti-tumor drug development. Therefore, they sought to provide novel photo-protected drugs that are inactive, while after photo-deprotection an active MDM2-inhibitor is liberated, taking advantage of the non-invasive nature of light.

The molecular design underlying the present invention was based on a recently developed MDM2 inhibitor, idasanutlin, which showed high potency, moderate selectivity and good bioavailability.[7,14,16] It was postulated that the m-methoxybenzoic acid group of the nutlin plays a potential role in binding affinity, cellular potency/stability and pharmacokinetic properties (see FIG. 1.a, marked red). Synthetic modification of the acid was hypothesized to render the nutlin derivative inactive. The possibility to alter the activity of idasanutlin by masking of this functional group was further supported by docking studies, which suggested that a potential interaction with Lys90 of MDM2 may be prevented in the protected compound (FIG. 1.b).

Encouraged by these preliminary docking studies, the inventors designed a photoresponsive nutlin prodrug (herein also referred to as "photonutlin") which shows a difference in activity between the protected and photo-deprotected forms. From the various types of PPG moieties known in the art[22], a coumarin scaffold was selected as the PPG of choice.

The novel photo-activatable MDM2 inhibitor, PPG-idasanutlin, was found to exert no functional effect on cellular outgrowth, but allows for the selective, non-invasive activation of anti-tumor properties upon irradiation with visible light demonstrating activation with micrometer, single cell precision. The generality of this method was demonstrated by growth inhibition of multiple cancer cell lines showing p53 stabilization and subsequent growth inhibition effects upon irradiation.

Figure 2:
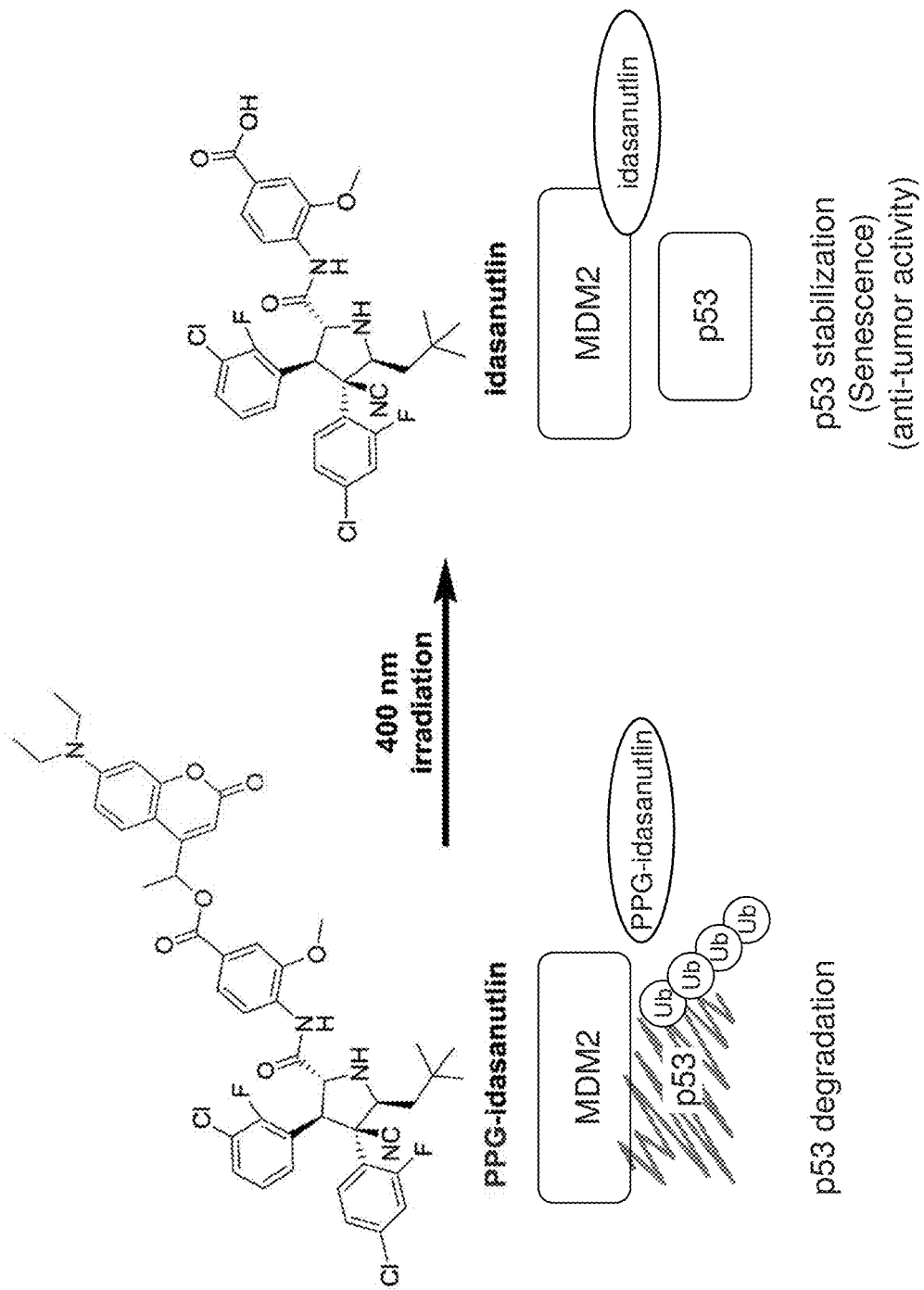
Figure 3A:
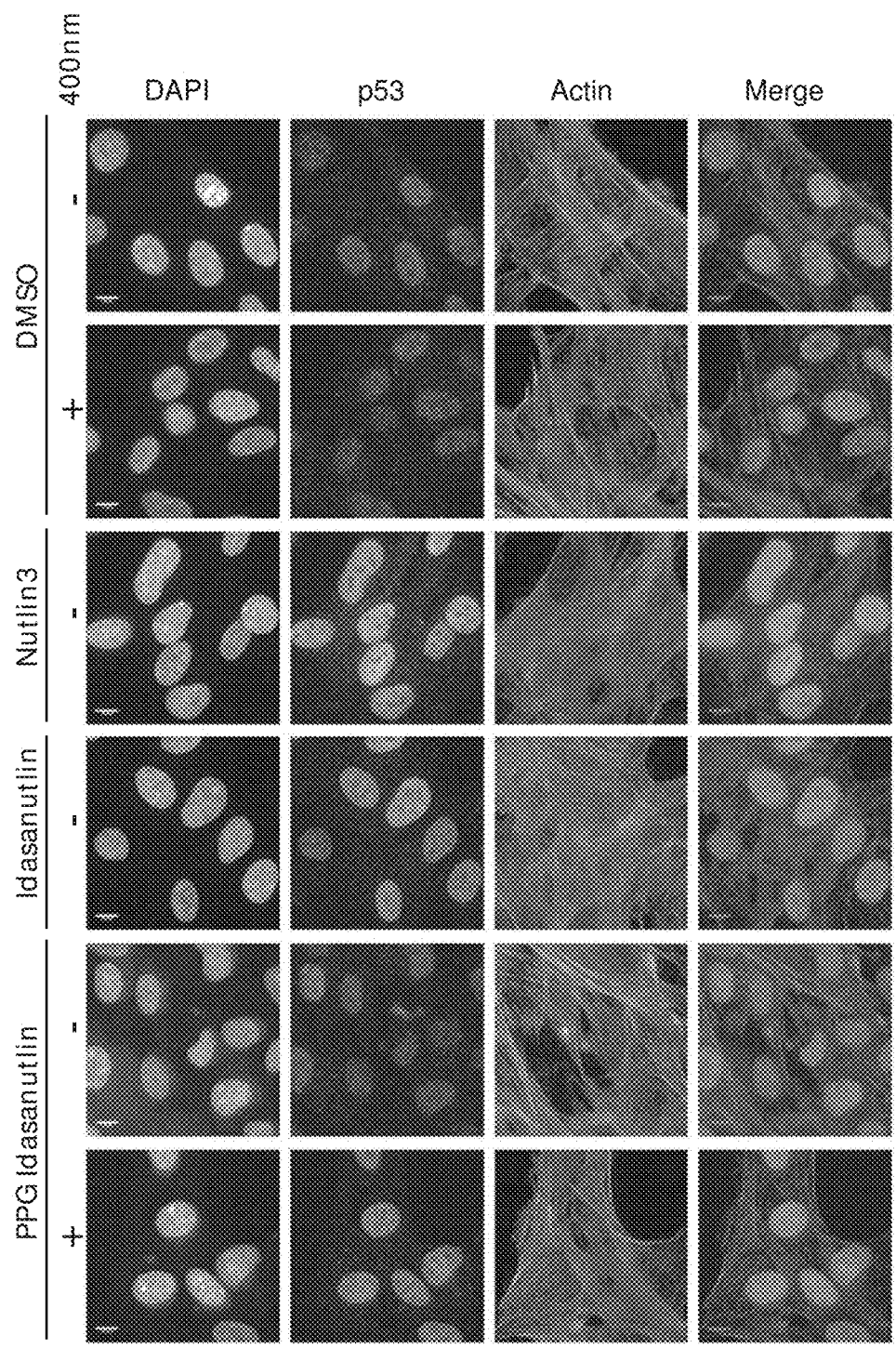
Figure 3B:
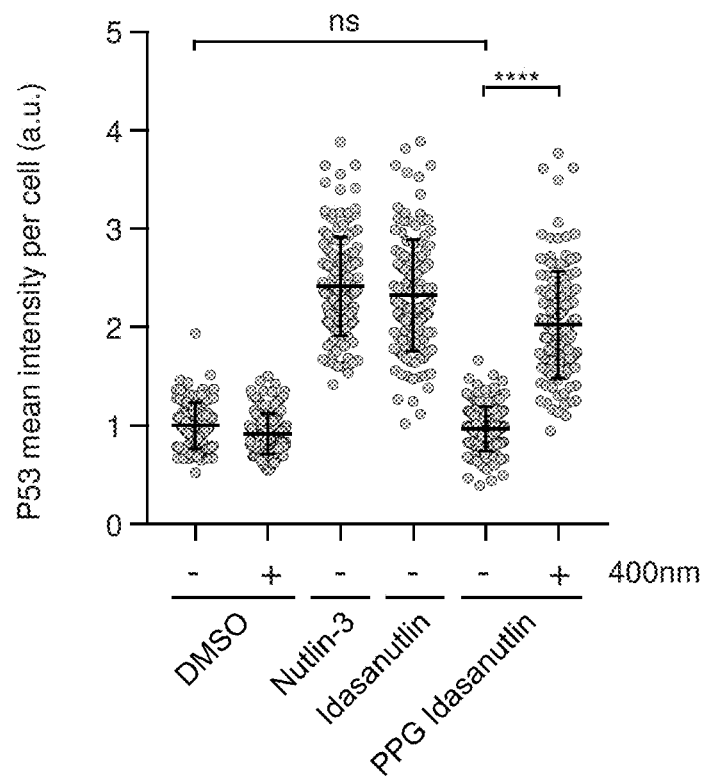
Figure 3C:
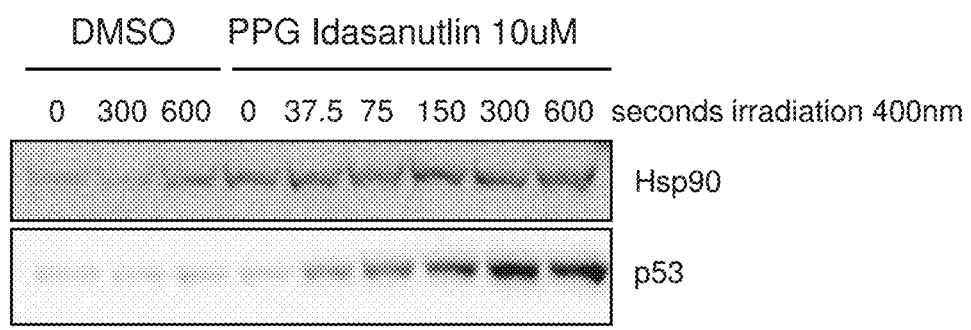
Figure 3D:
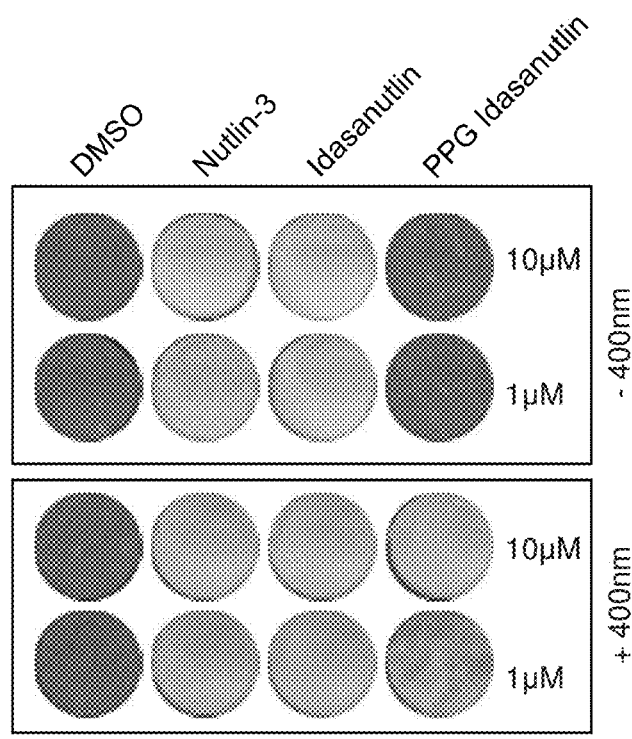
Figure 3E:
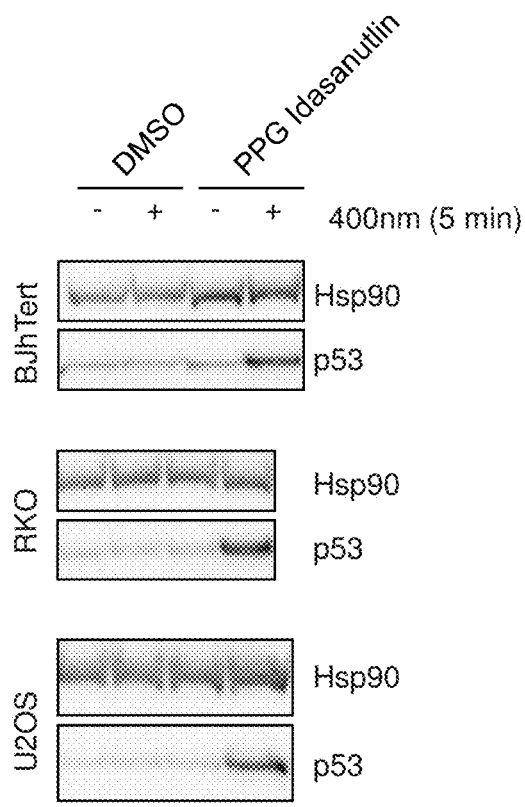
Figure 3F:
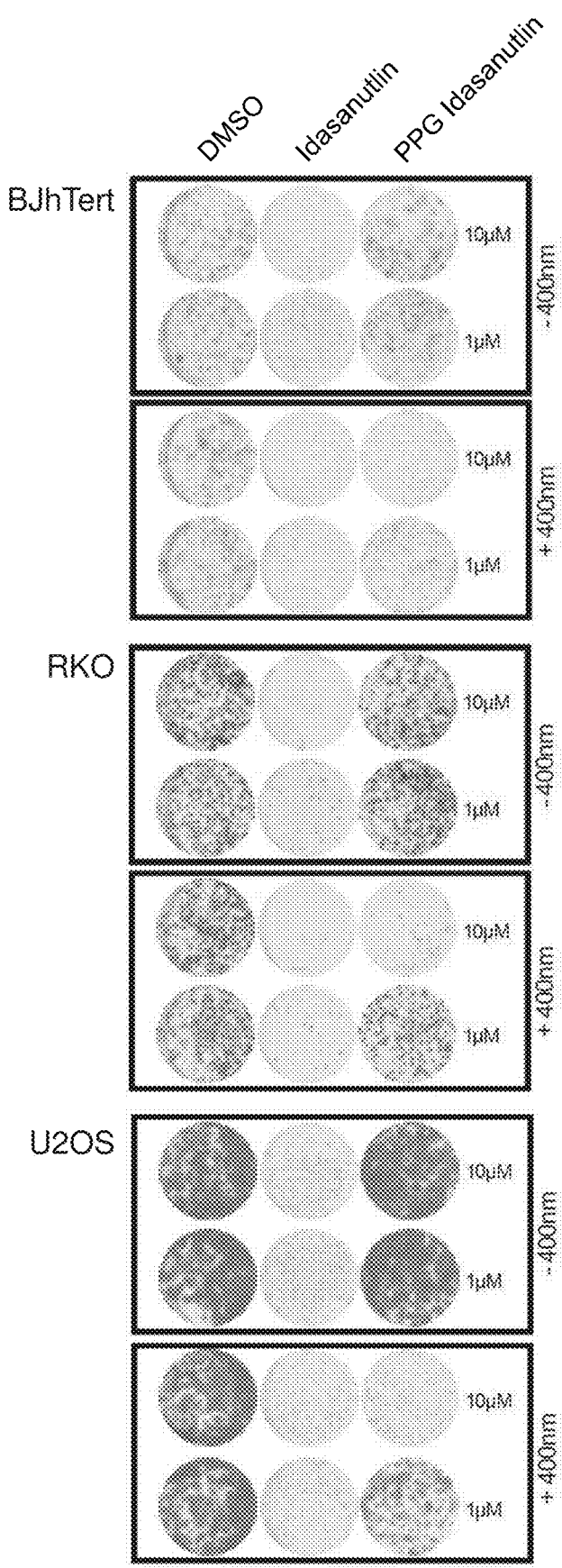

The principle of phototriggered p53 stabilization using a photonutlin of the invention is shown in FIG. 2. The exemplary inactive photonutlin (PPG-idasanutlin) is not capable of blocking the MDM2-p53 protein-protein interaction, resulting in p53 degradation. Photochemical release of idasanutlin prevents MDM2-p53 binding, thereby triggering senescence or cell death. The system described herein allows, for the first time, the selective light-activation of tumor-arresting p53 in living cells.

Accordingly, the invention provides a compound having the chemical structure of Formula I

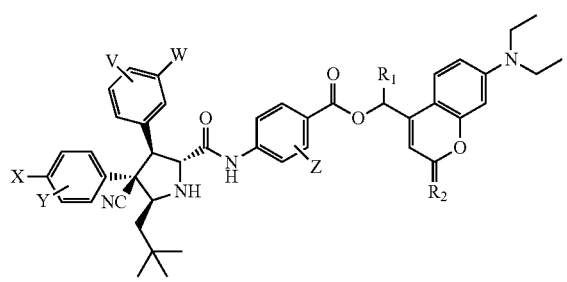

Formula I wherein

V is —H or —F;

W is —F, —Cl or —Br;

X is selected from the group consisting of H, F, Cl, Br, I, cyano, nitro, ethynyl, cyclopropyl, methyl, ethyl, isopropyl, vinyl and methoxy;

Y is one to four group(s) independently selected from the group consisting of —H, —F, —Cl, —Br, —I, —CN, —OH, nitro, lower alkyl, cycloalkyl, lower alkoxy, lower alkenyl, cycloalkenyl and lower alkynyl;

Z is —Cl, —F, —Br, —I or lower alkoxy;
$R_1$ is —H or —$CH_3$
$R_2$ is O, S or $C(CN)_2$
or a pharmaceutically acceptable salt thereof.

Also provided is a compound having the chemical structure

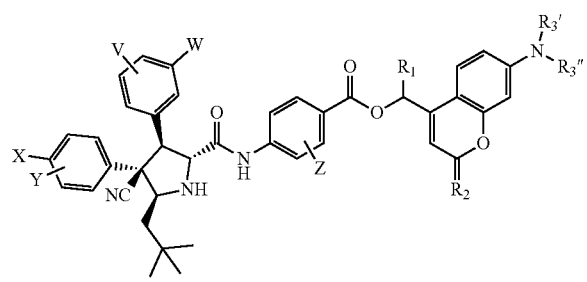

wherein the substituents X, Y, V, W, $R_1$ and $R_2$ are as defined herein above, and wherein $R_3{}'$ and $R_3{}''$ are moieties known in the art to enhance pharmacokinetic properties, e.g. solubility, of the compound, including polyethylene glycol (PEG) containing groups and carboxylic acids. $R_3{}'$ and $R_3{}''$ may be the same or different from each other. To facilitate synthesis of the compound, it is however preferred that $R_3{}'$ and $R_3{}''$ are identical. In one embodiment, $R_3{}'$ and $R_3{}''$ are independently selected from the group consisting of group consisting of lower alkoxy, substituted lower alkoxy, alkylamino, dialkylamino, glucuronic acid, hexoses, aminohexoses, pyranoses, aminoglycosides, natural and unnatural amino acids, —$OCH_2C(O)N(CH_3)_2$, —$(OCH_2CH_2)_n$—OH, —$OCH_2CH_2)_n$—$OCH_3$, —$OCH_2C(O)$—$(OCH_2CH_2)_n$—OH, —$OCH_2C(O)$—$(OCH_2CH_2)_n$—$OCH_3$, —$NH(CH_2CH_2O)_n$—$CH_3$, —$NH(CH_2CH_2O)_n$—H, —$OCH_2C(O)NH(CH_2CH_2O)_n$—$CH_3$, —$NH(OCH_2CH_2)_n$—$NH_2$, wherein n is from 3 to 60. In another embodiment, $R_3{}'$ and $R_3{}''$ are independently selected from the group consisting of group consisting of lower $C_1$-$C_4$ alkyl. For example, $R_3{}'$ and $R_3{}''$ are independently selected from methyl, ethyl and propyl.

A "pharmaceutically acceptable salt" is intended to mean those salts that retain the biological effectiveness and properties of the free acids and bases and that are not biologically or otherwise unacceptable for pharmaceutical use.

In a compound of the invention V is —H or —F, and W is —F, —Cl or —Br. In one embodiment, W is —Cl, and/or V is —F. The position of V on the phenyl ring carrying the W substituent in the meta-position can vary. For example, V can be in the ortho- or para-position, or both W and V may be in the meta-position. In a preferred aspect, V occupies the position next to the W substituent. For example, the phenyl carries —Cl at the meta-position and —F at the adjacent ortho-position.

X is selected from the group consisting of H, F, Cl, Br, I, cyano, nitro, ethynyl, cyclopropyl, methyl, ethyl, isopropyl, vinyl and methoxy. In one embodiment, X is a halogen selected from the group consisting of F, Cl, Br and I, preferably wherein X is —Cl or —F. In a specific aspect, X is —Cl. In another embodiment, X is cyano, nitro, ethynyl, cyclopropyl, methyl, ethyl, isopropyl, vinyl or methoxy.

Y is one to four group(s) independently selected from the group consisting of —H, —F, —Cl, —Br, —I, —CN, —OH, nitro, lower alkyl, cycloalkyl, lower alkoxy, lower alkenyl, cycloalkenyl and lower alkynyl. Preferably, Y is one group selected from the group consisting of —F, —Cl, —Br, —I, —CN, —OH, nitro, lower alkyl, cycloalkyl, lower alkoxy, lower alkenyl, cycloalkenyl and lower alkynyl.

The term "lower alkyl" refers to alkyl groups having from 1 to 6 carbon atoms, and in certain embodiments from 1 to 4 carbon atoms, Examples of alkyl groups include methyl, ethyl, n-propyl, i-propyl, n-butyl, s-butyl, t-butyl, n-pentyl, and s-pentyl. "Lower alkoxy" refers to any of the above lower alkyl groups attached to an oxygen atom. Typical lower alkoxy groups include methoxy, ethoxy, isopropoxy or propoxy, butyloxy. The term "lower alkenyl" as used herein means an unsaturated straight-chain or branched aliphatic hydrocarbon group containing one double bond and having 2 to 6, preferably 2 to 4 carbon atoms. The term "lower alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl and 3-butynyl.

The term "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated.

The Y substituent in a photonutlin provided herein is preferably selected from —F and —Cl, more preferably Y is —F. The position of Y on the phenyl ring can vary. Preferably, Y is at the ortho-position. For example, in one embodiment the invention provides a compound of the formula

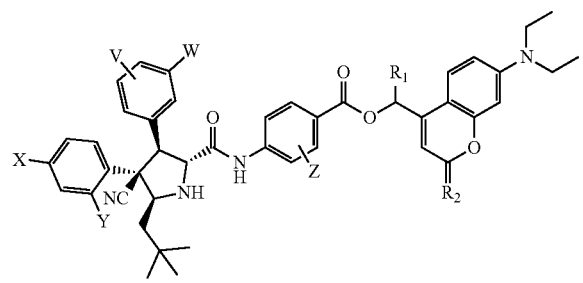

The Z substituent is —Cl, —F, —Br, —I or a lower alkoxy. In one embodiment, Z is —Cl, —F, —Br or —I, preferably —Cl. In another embodiment, Z is a lower alkoxy, preferably —$OCH_3$.

The R groups in the PPG moiety of the photonutlin can vary. $R_1$ is —H or —$CH_3$. For reasons of improved hydrolytic stability and increased rate of photocleavage, the PPG is a hydroxymethylcoumarin. Hence, in one embodiment $R_1$ is —$CH_3$.

$R_2$ can be O, S or $C(CN)_2$. Good results were obtained with a photonutlin wherein $R_2$ is O, which can be cleaved by illuminating at a wavelength of around 400 nm. However, it may be desirable for certain (clinical) applications to shift the wavelength for inducing photocleavage to the near-infrared (NIR) spectrum e.g. to achieve enhanced tissue penetration depth. To that end, the invention also provides photonutlins having a redshifted absorption. For example, $R_2$ in the PPG of a photonutlin of the invention can be S or $C(CN)_2$ to provide a compound that exhibits a maximum absorption in the range of about 470-500 nm (Fournier et al. Chem. Eur. J. 2013, 19, 17494-17507; Gandioso et al. ChemistryOpen. 2017 May 5; G(3):375-384)

In a specific embodiment, the invention provides a compound of the formula

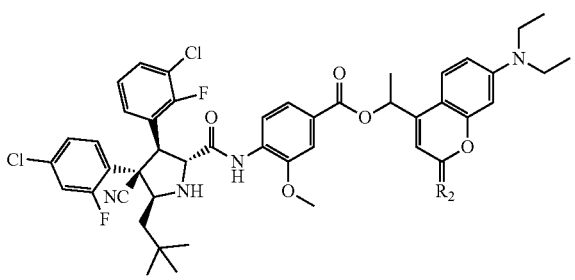

herein also referred to as "PPG-idasanutlin", or a pharmaceutically acceptable salt thereof.

A photonutlin of the present invention can be synthesized using standard methods known in the art of organic (medicinal) chemistry based on commercially available starting reagents. Example 1 herein below exemplifies the step-wise synthesis of the exemplary compound PPG-idasanutlin. Other photonutlin variants according to the invention may be prepared by methods known to those skilled in the art in a manner analogous to the general procedure outlined in Scheme 1 herein below.

The inventive photonutlin compounds or the pharmaceutically acceptable salts thereof may be administered as a pharmaceutical composition in any suitable pharmaceutical form recognizable to the skilled artisan. Therefore, a further aspect of the invention relates to a pharmaceutical composition comprising a compound as herein disclosed, and a pharmaceutically acceptable carrier, vehicle or diluent.

Suitable pharmaceutical forms include solid, semisolid, liquid or lyophilized formulations, such as tablets, powders, capsules, suppositories, suspensions and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

For example, the nutlin prodrug of the invention may be used in combination with one or more further (anti-cancer) drug, which further drug may but does not need to be in the form of a prodrug. Exemplary drugs for use in a combination therapy with a compound herein disclosed include pegylated interferon, dexamethasone, ixazomib, venetoclax, cytarabin, and monoclonal antibodies, such as atezolizumab.

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling and dissolving the ingredients as appropriate, to give the desired products for oral, parenteral, topical, intravaginal, intranasal, intrabronchial, intraocular, intraaural and/or rectal administration.

A dose of the pharmaceutical composition contains at least a therapeutically effective amount of the photonutlin compound and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 100 milligrams or less, and even more preferably about 70 milligrams or less, per kilogram of the host weight. The selected dose may be administered to a mammal, for example, a human patient in need of treatment mediated by inhibition of the Mdm2/p53 protein interaction, by any known method of administrating the dose including: topically, for example, as an ointment or cream; orally; rectally, for example, as a suppository; parenterally by injection; or continuously by intravaginal, intranasal, intrabronchial, intraaural or intraocular infusion. In one embodiment, the photonutlin is administered orally or by injection.

A compound according to the invention generally finds its use as photo-activatable inhibitor of the interaction between MDM2 and p53. The inhibition can be achieved in vitro, e.g. in a cell-based system, or in vivo.

Among others, the invention relates to a method of treating in a subject a disorder mediated by a p53-MDM2 interaction comprising administering to the subject a therapeutically effective amount of a pharmaceutical composition comprising a photonutlin as herein disclosed. For example, a disorder mediated by a p53-MDM2 is a cell proliferative disorder.

In a preferred embodiment, the invention provides a photonutlin for use in a method of treating cancer, in particular a solid tumors, more particularly a breast, colon, lung or prostate tumor. Also provided is a method of treating cancer, in particular a solid tumors, more particularly a breast, colon, lung or prostate tumor, comprising administering to a subject in need thereof a therapeutically effective amount of a prodrug compound of the invention.

The term "Therapeutically effective amount" refers to that amount of the prodrug sufficient to result (upon photocleavage) in amelioration of one or more symptoms of a disorder, or prevent advancement of a disorder, or cause regression of the disorder. For example, with respect to the treatment of cancer, in one embodiment, a therapeutically effective amount will refer to the amount of compound that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The actual amount of the prodrug compounds or salts to be administered will also vary based upon a number of factors, including the degree of inhibition desired, the characteristics of the mammalian tissue in which inhibition is desired, the metabolic stability and activity of the particular compound employed, the mode of administration and the mode of photoactivation. One skilled in the art may readily determine a suitable dosage according to methods known to the art. Preferably, the amount of compound administered is between 0.1 mg/kg body weight and 100 mg/kg body weight per day.

Other exemplary types of cancer that may be treated using the photonutlin as monotherapy or in a combination therapy include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, cervical cancer, uterine cancer, ovarian cancer, testicular cancer, thyroid cancer, astrocytoma, esophageal cancer, pancreatic cancer, stomach cancer, liver cancer, melanoma; carcinosarcoma, Hodgkin's disease, Wilms' tumor or teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The method may comprise administering the prodrug compound to a subject in need thereof, followed by selectively illuminating (also referred to in the art as "irradiating") with light at a predetermined time and/or location of the body of said subject, under conditions effective to convert said compound into a biologically active agent. Depending on the specific structure and light absorbing properties of the PPG, light at a desired wavelength is selected. Typically, light in the biocompatible visible spectrum is used, such as $\lambda \geq 400$ nm. In one embodiment, the prodrug compound is selectively activated using light in the range of about 400 to 700 nm. Depending on the tissue or bodily site to be illuminated, an optical probe or fiber, optionally being part of a LED system, may be used.

In a specific aspect, the invention provides a method of treating in a subject a disorder mediated by a p53-MDM2 interaction comprising administering to the subject a therapeutically effective amount of a pharmaceutical composition comprising PPG-idasanutlin as herein disclosed. The method may comprise administering PPG-idasanutlin to a subject in need thereof, followed by selectively illuminating with light at a wavelength of about 400 nm at a predetermined time and/or location of the body of said subject, under conditions effective to convert PPG-idasanutlin into the biologically active idasanutlin and the biologically inert PPG.

LEGEND TO THE FIGURES

FIG. 1: Strategy towards photocleavable nutlin derivatives. a) Idasanutlin, a potent MDM2 inhibitor allowing the stabilization of p53 levels in tumor cells. b) Molecular docking showcases the possible interaction with Lys90 as a potential site to alter the activity (PDB: 4JRG).[29] c) Irradiation of PPG-idasanutlin led to the formation of idasanutlin and PPG(6) as the sole products. d) Absorption spectra of PPG-idasanutlin, idasanutlin and PPG (6) in buffer. (TRIS, BIS-TRIS, MES, NaOAc, 25 mM each, pH=7.0) at 20 μM concentration. e) UV-vis spectra of PPG-idasanutlin upon exposure to 400 nm light showing a clean photochemical conversion (isosbestic point at 350 nm) to the desired products.

FIG. 2: A schematic representation of the principle behind phototriggered p53 stabilization. The photonutlin compound (PPG-idasanutlin) is not able to inhibit the MDM2-p53 protein-protein interaction, which results in p53 ubiquitylation and degradation. Irradiation with 400 nm light releases the active inhibitor idasanutlin which prevents MDM2-p53 binding and as a consequence increases the p53 level, leading to senescence or cell death.

FIG. 3: Functional p53 induction upon $\lambda$=400 nm irradiation in PPG-idasanutlin treated cells, a) RPE-1 cells were treated with indicated compounds (all 10 μM final) and fixed 4 h after 5 min (−/+400 nm) irradiation. Anti-p53 staining indicates p53 protein expression in the nucleus. DNA stained by DAPI and actin staining shows the cytoskeleton of the cell. b) Quantification of the mean p53 intensity per nucleus in cells treated as in (a). Error bars represent mean +sd, ****P<0.0001 (unpaired t-test), Dots represent individual cells, n>125 cells per condition combined from 2 independent experiments. c) Representative western blot showing p53 protein levels in cells 4 h after addition of DMSO or PPG-idasanutlin and irradiation for indicated time periods. Hsp90 is used as a loading control. d) Selective outgrowth disadvantage in RPE-1 cells 6 days after PPG-idasanutlin treatment +400 nm irradiation for 5 min. e) Representative Western blot showing p53 protein levels in three cell lines (U2OS, RKO, BJhTert) 4 h after indicated treatments. f) Selective outgrowth inhibition in indicated cell lines 6 days after PPG-idasanutlin treatment +400 nm irradiation for 5 min. In all the experiments <1% DMSO was used.

Figure 4:
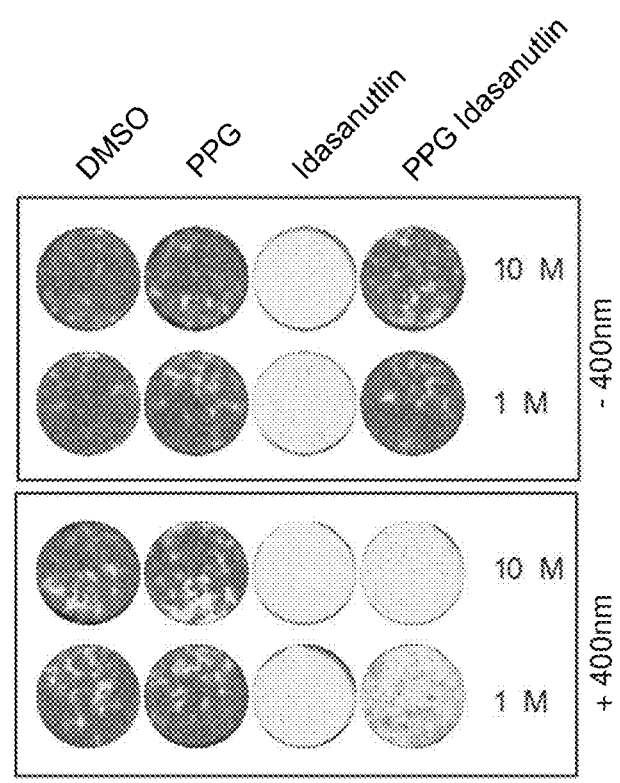

FIG. 4: Cell outgrowth experiments showing that PPG 6 (the photoproduct formed upon photocleavage of photonutlin) does not perturb cellular outgrowth.

Figure 5A:
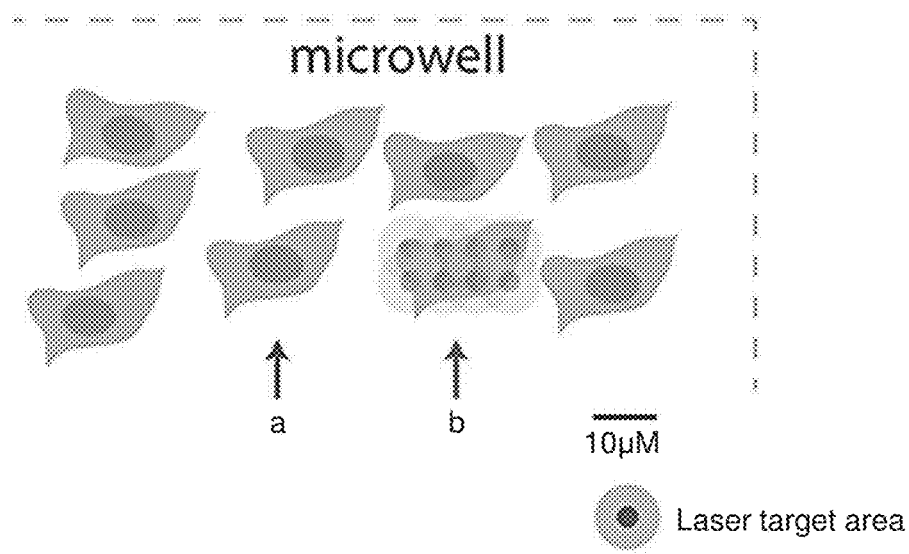
Figure 5B:
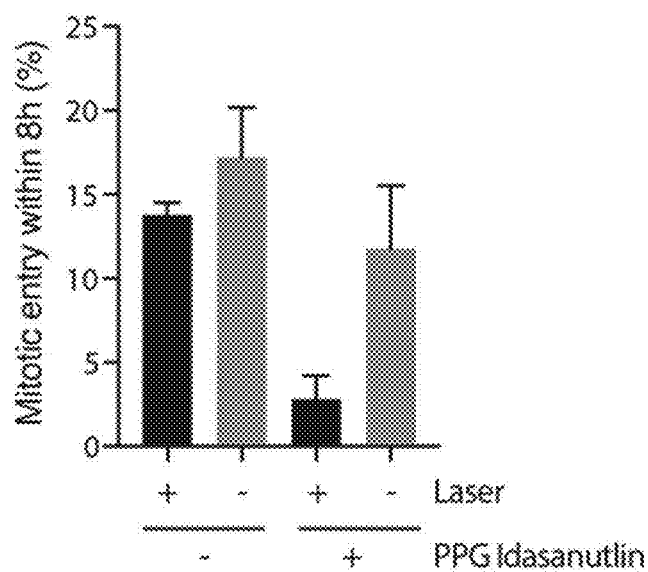

FIG. 5: Spatiotemporal control of PPG-idasanutlin. a) Schematic representation of microwell set-up for laser irradiation of individual RPE-1 cells to activate PPG-idasanutlin. Laser target area (represented. by red circle) for single pulse (0.1 sec irradiation at 5 um interspaced position) indicated with scale. Individual irradiated cells followed by measuring nuclear p53-venus levels (fluorescence) every 15 min for 3 h after laser irradiation. Approximately 200 cells in each microwell. b) Percentage of cells that divide within 8 h after indicated treatments. Mean±sem of three independent experiments. Error bars indicate 95% confidence intervals. c, d) p53-venus fluorescent signal in individual RPE-1 cells tracked over time after indicated treatments as represented in (a). Line-graphs represent mean of individual cells. n>42 cells per condition pooled from three independent experiments. *p<0.005, **p<0.0001 significance in 2-way anova interaction score.

EXPERIMENTAL SECTION

Materials and Methods

General. All chemicals for synthesis were Obtained from commercial sources and used as received unless stated otherwise.

Thin Layer Chromatography (TLC) was performed using commercial Kieselgel 60, F254 silica gel plates with fluorescence-indicator $UV_{254}$ (Merck, TLC silica gel 60 $F_{254}$). For detection of components, UV light at $\lambda$=254 nm or $\lambda$=365 nm was used. Alternatively, oxidative staining using aqueous basic potassium permanganate solution ($KMnO_4$) or aqueous acidic cerium phosphomolybdic acid solution (Seebach's stain) was used. Flash chromatography was performed on silica gel (Silicycle Siliaflash P60, 40-63 mm, 230-400 mesh). Drying of solutions was performed with MgSO$_4$ and volatiles were removed with a rotary evaporator. Nuclear Magnetic Resonance spectra were measured with an Agilent Technologies 400-MR (400/54 Premium Shielded) spectrometer (400 MHz). All spectra were measured at room temperature (22-24° C.). Chemical shifts for $^1$H- and $^{13}$C-NMR measurements were determined relative to the residual solvent peaks in ppm ($\delta_H$ 7.26 for CHCl$_3$, 2.50 for DMSO and 2.05 ppm for Acetone, $\delta_C$ 77.16 for CHCl$_3$ and 39.52 for DMSO). The following abbreviations are used to indicate signal multiplicity: s, singlet; d, doublet; t, triplet; q, quartet; m, multiplet; brs, broad signal. All $^{13}$C-NMR spectra are $^1$H-broadband decoupled. High-resolution mass spectrometric measurements were performed on a Thermo scientific LTQ Orbitrap XL with ESI ionization. For spectroscopic measurements, solutions in Uvasol® grade solvents were measured in a 10 mm quartz cuvette. UV-Vis absorption spectra were recorded on an Agilent 8453 UV-Visible absorption Spectrophotometer.

Cell Culture hTert-immortalized retinal pigment epithelium (RPE-1) cells (ATCC) and hTert-immortalized BJ cells were maintained in Dulbecco's Modified Eagle Medium/Nutrient Mixture F-12 (DMEM/F12, Gibco) supplemented with ultraglutamine, penicillin/streptomycin and 10% fetal calf serum. RPE-1 cells with a fluorescently tagged version of p53 (p53-venus) were a kind gift from the Lahav lab.[3] RKO colon carcinoma cells were maintained in Dulbecco's Modified Eagle Medium (DMEM, Gibco) supplemented with ultraglutamine, penicillin/streptomycin and 10% fetal calf serum. U2OS cells were maintained in Dulbecco's Modified Eagle Medium (DMEM, Gibco) supplemented with ultraglutamine, penicillin/streptomycin and 6% fetal calf serum.

Immunofluorescent Staining and Live Cell Imaging

RPE-1 cells were plated on coverslips at equal density and treated with indicated drugs before –/+irradiation (400 nm for 5 min). For immune fluorescent staining, cells were fixed 4 h after irradiation by wash out of the medium, single wash in phosphate-buffered saline (1× PBS) and incubation in 3.7% formaldehyde for 5 min. Next, fixed cells were permeabilized with 0.2% TritonX in 1× PBS for 5 min before blocking in 3% fetal bovine serum (BSA) in 1× PBS supplemented with 0.1% Tween (PBST) for 1 h (all at room temperature (RT)). Cells were incubated overnight at 4° C. with primary antibody in PBST with 3% BSA, washed three times with PBST, and incubated with secondary antibody and DAPI in PBST with 3% BSA for 2 h at RT. After a final three time wash with PBST coverslips were mounted on microscopic analysis slides using ProLong Gold antifade reagent (Thermo Fisher). The following antibodies were used: anti-p53 (sc-126, Santa Cruz, 1/1000), phalloidin (A12380, Molecular Probes, 1/1000) and goat anti-mouse/Alexa. 488 (A11029, Molecular Probes, 1/1000).

For live cell imaging, cells were grown in picovitro microwells covered by a silicon membrane[4] in Leibovitz's L-15 (Gibco) CO$_2$-independent medium supplemented with ultraglutamine, penicillin/streptomycin and 10% fetal calf serum. Images for both fixed slides and live cell imaging were obtained using a Delta Vision Elite (applied precision) equipped with a 60× 1.6 NA or 10× 0.75 NA lens (Olympus) and cooled CoolSnap CCD camera. Directed laser irradiation was performed using a brief (0.1 s) pulse of a 405 nm laser on the Delta Vision Elite microscope equipped with a X4 laser module (Applied Precision). Image analysis was done using ImageJ software. Automated single cell analysis from live cell imaging was done as described before.[5]

Western Blot

RPE-1 cells were plated at equal density in 6-well plates followed by indicated treatments –/+irradiation (400 nm for 5 min) 24 h later. Cells were fixed and collected 4 h after treatment by wash out of the medium, single wash in 1× PBS followed by addition of laemmli buffer (4% SDS, 20% glycerol and 0.125 M Tris HCl). Equal amounts of proteins were separated by SDS-PAGE electrophoresis followed by semi-dry transfer to a nitrocellulose membrane. Membranes were blocked in 5% milk in PBST for 1 h at RT before overnight incubation with primary antibody in PBST with 3% BSA at 4° C. Membranes were washed 3 times with PBST followed by incubation with secondary antibody in PBST with 5% milk for 2 h at RT. Antibody staining was visualized using ECL (GE Healthcare). The following primary antibodies were used: anti-p53 (sc-126, Santa Cruz, 1/1000), anti-Cdk4 (C-22) (se-260, Santa Cruz, 1/1000). Peroxidase-conjugated-goat anti-mouse (P0447 DAKO, 1/1000) and goat anti-rabbit (P448 DAKO, 1/1000) were used as secondary antibodies.

Clonogenic Outgrowth

Cells were plated at equal amounts (1000 cells per well) in a 24-wells plate followed by indicated treatments –/+irradiation (400 nm for 5 min) 24 h later. Cells were cultured under normal cell culture conditions for 6 days to allow colony outgrowth. Plates were fixed using 99.8% ice-cold methanol (Honeywell) for 10 min at RT. After a 1 time wash in H$_2$O, cells were incubated in 0.2% crystal violet (Sigma) in H$_2$O for at least 3 h at RT to stain cellular outgrowth.

Example 1: Synthesis of PPG-idasanutlin

Scheme 1 depicts the overall synthesis of PPG-idasanutlin.

Scheme 1

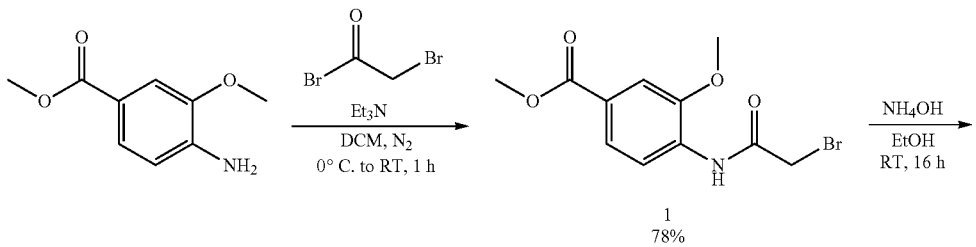

1
78%

-continued
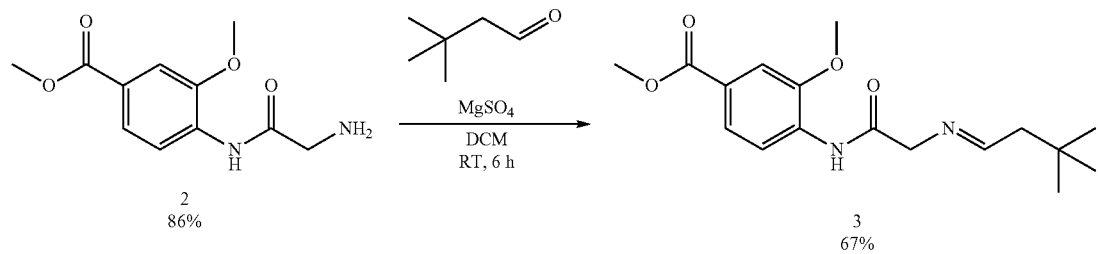
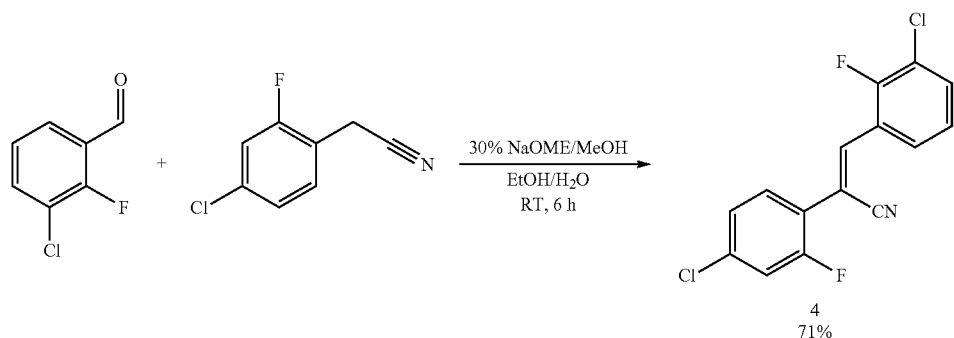
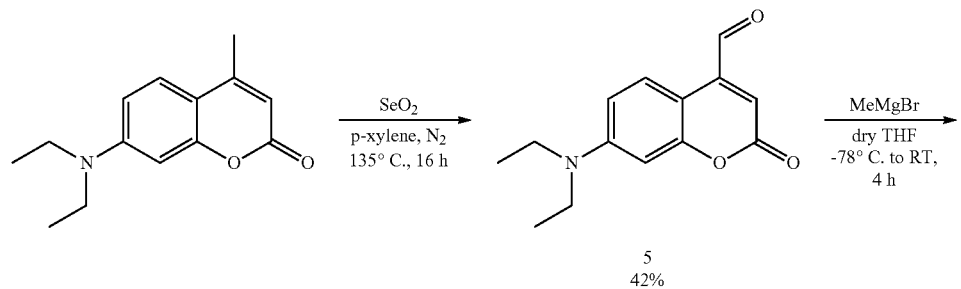
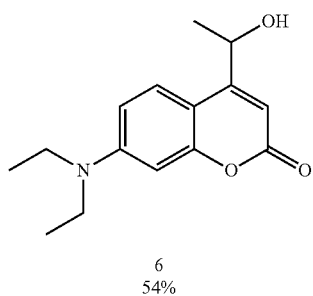

-continued
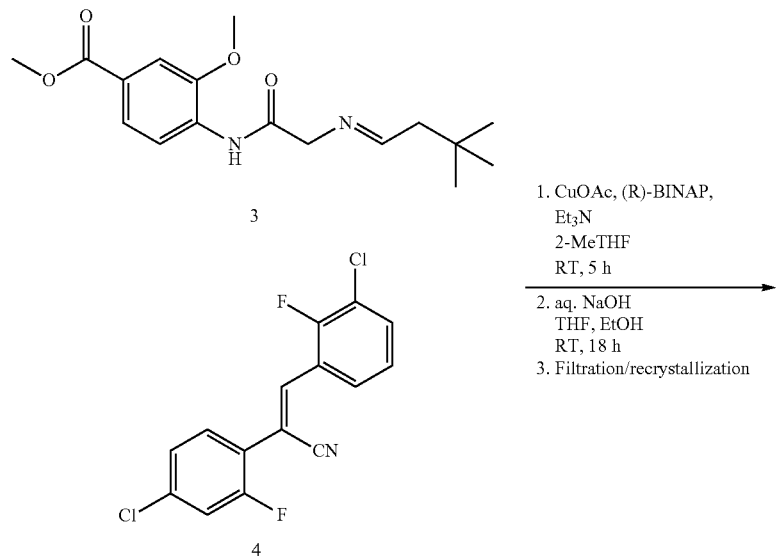
1. CuOAc, (R)-BINAP, Et₃N
   2-MeTHF
   RT, 5 h
2. aq. NaOH
   THF, EtOH
   RT, 18 h
3. Filtration/recrystallization
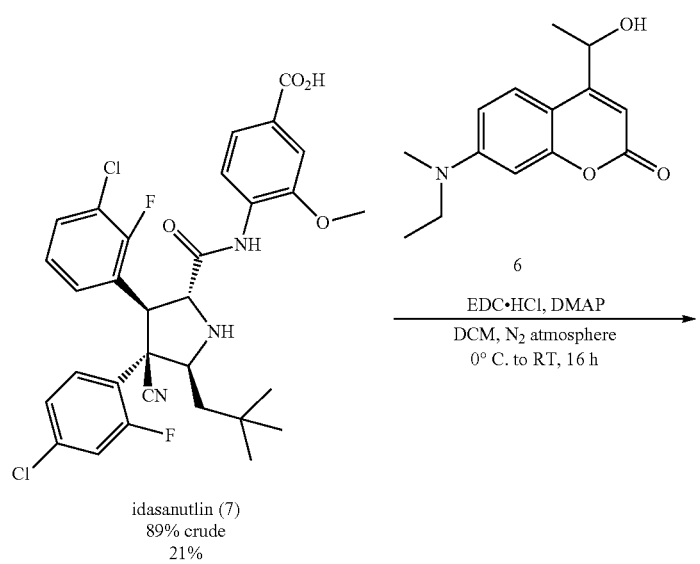
idasanutlin (7)
89% crude
21%
EDC·HCl, DMAP
DCM, N₂ atmosphere
0° C. to RT, 16 h

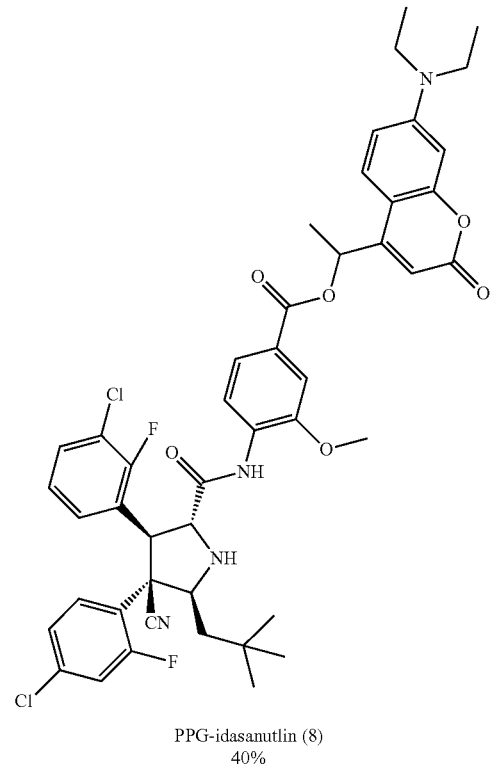 [SMILES: CCN(CC)c1ccc2c(C(C)OC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)cc(=O)oc2c1]

PPG-idasanutlin (8)
40%

Example 1A: Synthesis of methyl 4-(2-bromoacetamido)-3-methoxybenzoate (1)

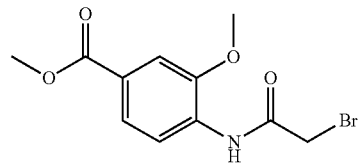 [SMILES: COC(=O)c1ccc(NC(=O)CBr)c(OC)c1]

To a solution of methyl 4-amino-3-methoxybenzoate (500 mg, 2.76 mmol) in DCM (18 mL) at 0° C. was added Et$_3$N (768 µL, 5.52 mmol) under N$_2$ atmosphere. Subsequently, 2-bromoacetyl-bromide (610 mg, 263 µL, 3.03 mmol) was slowly added and the reaction mixture was stirred for 45 min at 0° C. Subsequently, 1M aq. HCl (10 mL) was added and the solution was extracted with DCM (2×20 mL). The organic layers were washed with sat. aq. NaHCO$_3$ (20 mL) and brine (20 mL) and dried (MgSO$_4$). Evaporation of the volatiles in vacuo and recrystallization from EtOH and MeCN yielded the pure product (654 mg, 78%).

$^1$H NMR (400 MHz, CDCl$_3$): δ 8.95 (s, 1H), 8.41 (d, J=8.5 Hz, 1H), 7.70 (dd, J=8.5, 1.8 Hz, 1H), 7.57 (d, J=1.8 Hz, 1H), 4.04 (s, 2H), 3.98 (s, 3H), 3.91 (s, 3H).

$^{13}$C NMR (100 MHz, CDCl$_3$): δ 166.6, 163.5, 147.7, 131.0, 125.9, 123.2, 118.4, 110.8, 56.1, 52.1, 29.5.

Example 1B: Synthesis of methyl 4-(2-aminoacetamido)-3-methoxybenzoate (2)

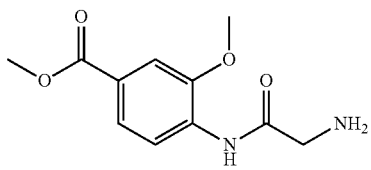 [SMILES: COC(=O)c1ccc(NC(=O)CN)c(OC)c1]

To an aqueous solution of NH$_3$ (20 mL) was slowly (dropwise) added 1 (1.40 g, 4.63 mmol) in EtOH (45 mL) in 30 min. Subsequently, the reaction was stirred for 5 h at RT and extracted with DCM (3×50 mL). The organic layers were washed with brine (3×50 mL) and dried (MgSO$_4$). Evaporation of the volatiles in vacuo yielded the pure product (945 mg, 86%).

$^1$H NMR (400 MHz, CDCl$_3$): δ 10.00 (s, 1H), 8.52 (d, J=8.5 Hz, 1H), 7.69 (dd, J=8.4, 1.8 Hz, 1H), 7.56 (d, J=1.8 Hz, 1H), 3.96 (s, 3H), 3.90 (s, 3H), 3.52 (s, 2H). Data in accordance with literature.

$^{13}$C NMR (100 MHz, CDCl$_3$): δ 171.2, 166.7, 147.7, 131.6, 124.9, 123.3, 118.3, 110.7, 55.9, 52.0, 45.6.

Example 1C: Synthesis of methyl (E)-4-(2-((3,3-dimethylbutylidene)amino)acetamido)-3-methoxybenzoate (3)

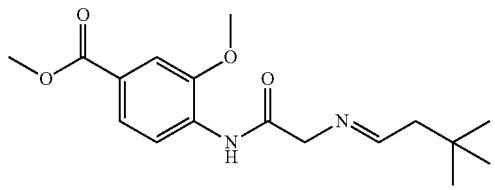 [SMILES: COC(=O)c1ccc(NC(=O)C/N=C/CC(C)(C)C)c(OC)c1]

To a solution 2 (300 mg, 1.26 mmol) in dry DCM (10 mL) under N2 atmosphere was added 3,3-dimethylbutanal (174 mL, 1.38 mmol) and MgSO4 (227 mg, 1.89 mmol) and the resulting suspension was stirred for 16 h at RT. Subsequently, the suspension was filtered and the residue washed with DCM (10 mL). Evaporation of the filtrate yielded the crude product (302 mg, 67%) as a yellow oil which was used in the next step without further purification.

$^1$H NMR (400 MHz, CDCl$_3$): δ 9.45 (s, 1H), 8.52 (d, J=8.5 Hz, 1H), 7.84 (tt, J=5.6, 1.5 Hz, 1H), 7.69 (dd, J=8.4, 1.8 Hz, 1H), 7.55 (s, 1H), 4.21 (s, 2H), 3.93 (s, 3H), 3.90 (s, 3H), 2.27 (d, J=5.7 Hz, 2H), 1.03 (s, 9H).

Example 1D: Synthesis of (Z)-3-(3-chloro-2-fluorophenyl)-2-(4-chloro-2-fluorophenyl)acrylonitrile (4)

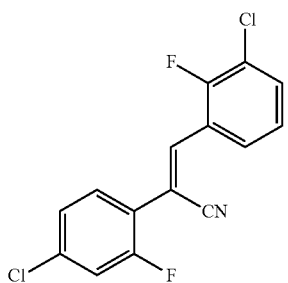 [SMILES: N#C/C(=C\c1cccc(Cl)c1F)c1ccc(Cl)cc1F]

To a solution of 3-chloro-2-fluorobenzaldehyde (468 mg, 2.95 mmol) and 2-(4-chloro-2-fluorophenyl)acetonitrile (500 mg, 2.95 mmol) in EtOH (10 mL) and H$_2$O (40 µL) was added NaOEt (10.0 mg, 0.15 mmol) and subsequently the reaction mixture was stirred for 3 h at RT. The resulting suspension was filtered and the precipitate was washed with EtOH. Evaporation in vacuo yielded the crude product which was dissolved in DCM (10 mL) and washed with brine (3×20 mL) and dried (MgSO4). Evaporation of the volatiles yielded the pure product (650 mg, 71%) as a white solid.

$^1$H NMR (400 MHz, DMSO-d$_6$): δ 7.97 (td, J=6.8, 1.4 Hz, 1H), 7.88 (s, 1H), 7.77 (ddd, J=8.6, 7.4, 1.6 Hz, 1H), 7.72 (t, J=8.5 Hz, 1H), 7.66 (dd, J=11.0, 2.1 Hz, 1H), 7.47 (ddd, J=8.4, 2.1, 0.8 Hz, 1H), 7.42 (td, J=8.0, 1.1 Hz, 1H), $^{19}$F NMR (376 MHz, DMSO-d$_6$): δ −111.41 (dd, J=11.1, 8.6 Hz), −115.42 (t, J=7.0 Hz).

Example 1E: Synthesis of 7-(diethylamino)-2-oxo-2H-chromene-4-carbaldehyde (5)

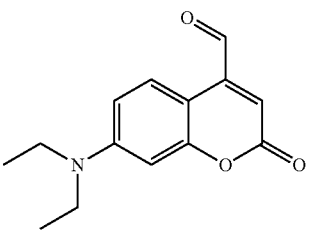 [SMILES: CCN(CC)c1ccc2c(C=O)cc(=O)oc2c1]

A solution of 7-(diethylamino)-4-methyl-coumarin (500 mg, 2.16 mmol) and SeO$_2$ (480 mg, 4.32 mmol) in p-xylene (20 mL) was heated to 150° C. for 16 h under N2 atmosphere in the dark. Subsequently, the solution was filtered while hot and concentrated in vacuo. Purification by column chromatography (DCM) yielded the pure product (223 mg, 42%) as an orange viscous oil.

$^1$H NMR, (400 MHz, CDCl$_3$): δ 10.03 (s, 1H), 8.31 (d, J=9.2 Hz, 1H), 6.63 (dd, J=9.2, 2.6 Hz, 1H), 6.53 (d, J=2.6 Hz, 1H), 6.45 (s, 1H), 3.43 (q, J=7.1 Hz, 4H), 1.22 (t, J=7.1 Hz, 6H).

Example 1F: Synthesis of 7-(diethylamino)-4-(1-hydroxyethyl)-2H-chromen-2-one (6)

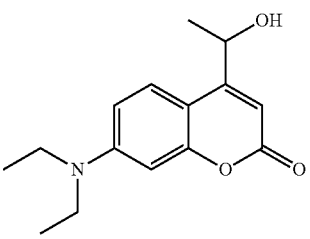 [SMILES: CCN(CC)c1ccc2c(C(C)O)cc(=O)oc2c1]

To a solution of 5 (220 mg, 0.89 mmol) in dry THF (8 mL) under N2 atmosphere at −78° C. was slowly added MeMgBr in THF (3M, 534 µL, 1.60 mmol) and the reaction mixture was stirred for 2.5 h at −78° C. in the dark. Subsequently, sat. aq. NH$_4$Cl was added (10 mL) and the mixture was allowed to warm to RT. The organic layer was separated and the aqueous layer extracted with EtOAc (2×10 mL). The combined organic layers were washed with brine (20 mL), dried and evaporated in vacuo to yield the crude product. Column chromatography (pentane:acetone, 3:1) yielded the pure product (125 mg, 54%) as an orange solid.

$^1$H NMR (400 MHz, CDCl$_3$): δ 7.42 (d, J=9.0 Hz, 1H), 6.57 (dd, J=9.0, 2.7 Hz, 1H), 6.52 (d, J=2.6 Hz, 1H), 6.27 (d, J=0.9 Hz, 1H), 5.22-5.09 (m, 1H), 3.41 (q, J=7.1 Hz, 4H), 1.57 (d, J=4.7 Hz, 3H), 1.21 (t, J=7.1 Hz, 6H).

Example 1G: Synthesis of Idasanutlin (4-((2R,3S, 4R,5S)-3-(3-chloro-2-fluorophenyl)-4-(4-chloro-2-fluorophenyl)-4-cyano-5-neopentylpyrrolidine-2-carboxamido)-3-methoxybenzoic acid (7))

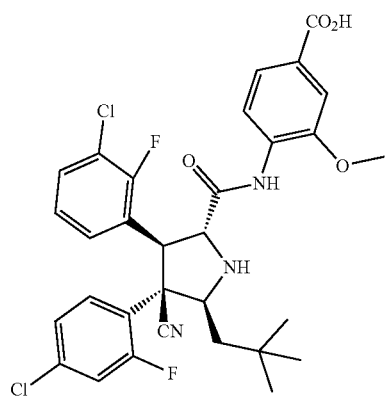 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

A solution of CuOAc (0.56 mg, 4.58 μmol) and R-BINAP (3.0 mg, 4.81 μmol) in THF (5 mL) was slowly added to a suspension of 3 (302 mg, 0.95 mmol) and 4 (279 mg, 0.90 mmol) in THF (5 ml) under $N_2$ atmosphere at RT. Subsequently, $Et_3N$ (123 mL, 0.88 mmol) was added and the resulting mixture was stirred for 5 h at RT. Next, THF (10 mL) was added and the resulting solution was washed twice with aq. $NH_4OAc$ (10 mL, 10% w/w) and brine (10 mL). Subsequently, the organic layers were evaporated and the crude product was dissolved in THF (7 mL) and EtOH (3 mL). 2.5M aq. NaOH (1 mL) was added and the mixture was stirred for 18 h at RT. The solution was acidified with AcOH to pH=6.0 and the volatiles were partially evaporated (2 mL). After addition of $H_2O$ (10 mL) the precipitate was filtered to give the crude product (493 mg, 89%) as an off-white solid. Subsequent enantio-enrichment and purification was performed by crystallization. The crude product (493 mg) was dissolved in THF (6 mL) and heated to 65° C. Subsequently EtOAc (2 mL) was added and the resulting solution was heated for 15 min after which it was cooled to RT and filtered. The residue was washed with EtOAc (5 mL) and the filtrate evaporated in vacuo. The crude product was dissolved in MeCN (7 mL) and heated to 80° C. after which it was slowly cooled to 10° C. The precipitate was filtered yielding the pure product (118 mg, 21%) as a white solid.

$^1H$ NMR (400 MHz, DMSO-$d_6$): δ 12.85 (s, 1H), 10.45 (s, 1H), 8.35 (d, J=8.8 Hz, 1H), 7.71 (t, J=7.3 Hz, 1H), 7.62-7.50 (m, 4H), 7.44-7.28 (m, 3H), 4.66-4.52 (m, 2H), 4.37 (s, 1H), 3.91-3.85 (m, 4H), 1.63 (dd, J=14.2, 9.9 Hz, 1H), 1.25 (d, J=14.2 Hz, 1H), 0.96 (s, 9H).

HR-MS (ESI, [M+H]$^+$): Calcd. for $C_{31}H_{31}Cl_2F_2N_3O_4$: 616.1576; Found: 616.1575

Example 1H: Synthesis of PPG-idasanutlin (1-(7-(diethylamino)-2-oxo-2H-chromen-4-yl)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate ((8))

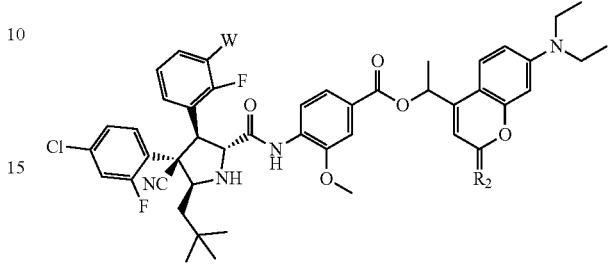

To a solution of 7 (100 mg, 0.16 mmol) and 6 (47 mg, 0.18 mmol) in dry DCM (3 mL) under $N_2$ atmosphere was added EDC.HCl (37 mg, 0.19 mmol) and DMAP (5 mg, 0.04 mmol) at 0° C. Subsequently, the reaction mixture was allowed to warm to RT and stirred for 16 h. Subsequently, DCM (10 mL) was added and the resulting solution was washed with 0.5M aq. HCl (3×10 mL), sat. aq. NaHCO3 (2×10 mL) and brine (10 mL) and dried (MgSO4). All the volatiles were evaporated to yield the crude product (135 mg). Column chromatography (pentane:ethyl acetate, 3:1) yielded the pure product (55 mg, 40%) as a bright yellow solid.

$^1H$ NMR (400 MHz, DMSO-$d_6$): δ 10.51 (s, 1H) 8.42 (d, J=7.0 Hz, 1H), 7.74-7.66 (m, 3H), 7.62 (s, 1H), 7.59-7.49 (m, 2H), 7.42-7.31 (m, 3H), 6.72 (d, J=9.3 Hz, 1H), 6.54 (s, 1H), 6.24 (q, J=6.6 Hz, 1H), 6.02 (s, 1H), 4.64-4.55 (m, 2H), 4.44-4.36 (m, 1H), 3.99-3.90 (m, 4H), 3.42 (q, J=6.7 Hz, 4H), 1.65 (d, J=6.8 Hz, 3H), 1.63-1.60 (m, 1H), 1.25 (d, J=14.3 Hz, 1H), 1.11 (t, J=6.9 Hz, 6H), 0.96 (s, 9H).

$^{13}C$ NMR (151 MHz, DMSO-$d_6$): δ 171.8, 164.7, 161.3, 160.8, 159.1, 156.8, 156.7, 156.6, 155.2, 150.9, 148.1, 135.2, 132.1, 131.4, 130.5, 129.1, 126.3, 126.1, 125.7, 124.5, 123.5, 120.0, 119.6, 118.1, 117.7, 111.5, 109.4, 105.3, 103,8, 97.5, 68.8, 65.1, 63,7, 56.3, 50.6, 44,4, 44.3, 30.5, 29,9, 21.2, 12.7.

$^{19}F$ NMR (376 MHz, DMSO-$d_6$): δ −108.31 (dd, J=12.2, 8.8 Hz), −120.95. HR-MS (ESI, [M+H]+): Calcd. for $C_{46}H_{47}Cl_2F_2N_4O_6$: 859.2835; Found: 859.2841

Example 2: Photochemical Behavior of Photonutlin

Following the synthesis of PPG-idasanutlin as described in Example 1, its photochemical behavior under physiological conditions was investigated, UV-vis spectroscopy and UPLC-MS measurements were performed in aqueous buffer at pH=7.0. Upon photodeprotection with λ=400 nm light, solely the formation of idasanutlin and hydroxycoumarin was observed. See FIG. 2. The rate of photocleavage proved to be high, allowing the major photorelease of idasanutlin within 5 min of irradiation, with a 0.1% quantum yield. Moreover, no significant spontaneous hydrolysis of PPG-idasanutlin for >24 h in buffer at room temperature was observed (data not shown). Together, these findings demonstrate the application of PPG-idasanutlin under physiological assay conditions using short irradiation times with biocompatible visible (>400 nm) light.

Example 3: Biological Activity of Photonutlin

Next, the biological activity of PPG-idasanutlin was investigated. Initial studies aimed at confirming a difference in p53 activation upon $\lambda$=400 nm light exposure after addition of the protected idasanutlin derivative (PPG-idasanutlin). To that end, non-transformed, p53-proficient retinal pigment epithelial cells (RPE-1) were treated with either DMSO (control), nutlin-3, idasanutlin or PPG-idasanutlin, followed by −/+irradiation with 400 nm light (FIG. 3). Immunofluorescent staining revealed a significant increase in nuclear p53 protein levels in cells 4 h after addition of nutlin-3 or idasanutlin, regardless of the irradiation with 400 nm light.

Importantly, treatment with PPG-idasanutlin only resulted in a significant increase in p53 protein level when these cells were irradiated with 400 nm light (photorelease of idasanutlin, see FIG. 3.a,b). To examine the level of control over the dose-response of idasanutlin (employing PPG-idasanutlin), p53 protein levels in RPE-1 cells were determined by immunostaining after both increasing duration of 400 nm light irradiation and varying doses of PPG-idasanutlin (FIG. 3.c). The clear dose-response dependent accumulation of p53 protein shows the highly effective light controllable dose responsiveness of the biological effect using PPG-idasanutlin (FIG. 3.c).

Example 4: Growth Inhibition by Photonutlin

Subsequently, the functional ability of PPG-idasanutlin to photocontrol growth of rapidly dividing cells was investigated. Colony outgrowth of RPE-1 cells treated with PPG-idasanutlin was selectively blocked after irradiation with 400 nm, while irradiation did not perturb outgrowth of DMSO treated cells (FIG. 3.d).This showcases the use of 400 nm light in living systems as a valid approach to photocontrol biological function. It should be emphasized that in the outgrowth experiment seen in FIG. 3.d, treatment of cells with PPG-idasanutlin without 400 nm irradiation did not show any growth inhibition, confirming the lack of inherent activity of the protected idasanutlin. Hence, PPG-idasanutlin has no functional effect on p53 stabilization nor compromises cellular outgrowth.[33]

To verify whether (re-)activation of p53 by our light controllable PPG-idasanutlin is more generally applicable and not dependent on the non-transformed RPE-1 cells used in these experiments, additional non-transformed (BJ-hTert) and tumor (RKO (colon carcinoma), U2OS (osteosarcoma)) cell lines were included for follow-up analysis. Selective stabilization of p53, after treatment with photonutlin and light irradiation, was observed in all cell lines tested (FIG. 3.e). The light-controlled p53 activation invariably led. to a dramatic reduction in cellular outgrowth (FIG. 3.f) proving the possibility to control tumor cellular growth using photonutlin and light.

Furthermore, it could be demonstrated that the PPG photoproduct formed after photocleavage does not perturb cellular outgrowth (FIG. 4).

Example 5: Spatiotemporal Control of p53 Stabilization by Photonutlin

To demonstrate the spatiotemporal control of the designed system we sought to investigate the selective enhancement of p53 levels in individual RPE-1 cells within a cell population using light irradiation. Using RPE-1 cells that stably expressed a venus-tagged version of p53 (p53-venus), p53 protein accumulation could be tracked with high time-resolution in individual cells by live-cell microscopy. RPE p53-venus cells were grown in 620 μm wide microwells and a 405 nm laser was used to irradiate individual cells in the colony with a single 0.1 second pulse at 5 μm inter spaced positions to acquire micrometer precision (FIG. 5.a). To determine the functionality of the high spatiotemporal control obtained in this set-up, cell cycle progression was monitored in single cells following laser activation of PPG-idasanutlin (photorelease of idasanutlin). Functional p53 activation will halt cell division, causing fewer cells to pass through mitosis.[9] Indeed, the percentage of cells that divide within 8 h after the indicated treatment strongly drops in cells that were irradiated after treatment with photonutlin (FIG. 5.b). This shows that a specific cellular fate can be induced at single-cell resolution by laser irradiation as presented in FIG. 5.a.

Quantification of the nuclear p53-venus signal at 15 min intervals in single cells treated with PPG-idasanutlin revealed the selective stabilization of p53 protein following irradiation with the 405 nm laser (FIG. 5.c). A significantly lesser extent of p53 stabilization was detectable in neighbouring cells that were not irradiated by the 405 nm laser (FIG. 5.c). The limited stabilization of the non-irradiated neighbouring cells is most likely explained by diffusion of activated photonutlin within the excess of liquid cell culture medium in this 2D cell culture set-up. In contrast, p53 stabilization was completely absent in non-irradiated cells from adjacent wells at micrometer distance, where diffusion could not take place. In addition, p53 levels did not increase due to laser-induced damage to the cells, since p53 levels were unaltered in cells following an identical irradiation protocol in absence of PPG-idasanutlin (FIG. 5.d).

Together these results show the selective activation of PPG-idasanutlin resulting in the release of idasanutlin, using an extremely short (0.1 sec) pulse of 405 nm laser irradiation at micrometer, single-cell resolution, which offers promising opportunities for applications of photonutlins in a 3D setting like (tumor) tissue.

REFERENCES (1) Stewart, B.; Wild, C. World Cancer Report 2014 http://publications.iarc.fr/Non-Series-Publications/World-Cancer-Reports/World-Cancer-Report-2014 (accessed Jun. 16, 2017).
(2), Moslehi, J. J. Cardiovascular Toxic Effects of Targeted Cancer Therapies. *N. Engl. J. Med.* 2016, 375, 1457-1467.
(3) Bild, A. H.; Yao, G.; Chang, J. T.; Wang, Q.; Potti, A. Chasse, D.; Joshi, M.-B.; Harpole, D.; Lancaster, J. M.; Berchuck, A.; Olson Jr, J. A.; Marks, J. R.; Dressman, H. K.; West, M.; Nevins, J. R. Oncogenic Pathway Signatures in Human Cancers as a Guide to Targeted Therapies. *Nature* 2006, 439, 353-357.
(4) van't Veer, L. J.; Bernards, R. Enabling Personalized Cancer Medicine through Analysis of Gene-Expression Patterns. *Nature* 2008, 452, 564-570.
(5) Vogelstein, B.; Kinzler, K. W. P53 Function and Dysfunction. *Cell* 1992, 70, 523-526.
(6) Kastenhuber, E. R.; Lowe, S. W. Putting P53 in Context. *Cell* 2017, 170, 1062-1078.
(7) Lakoma, A.; Barbieri, E.; Agarwal, S.; Jackson, J.; Chen, Z.; Kim, Y.; Mcvay, M.; Shohet, J.; Kim, E. The MDM2 Small-Molecule Inhibitor RG7388 Leads to Potent Tumor Inhibition in P53 Wild-Type Neuroblastoma. *Cell Death Discov.* 2015, 1, 15026

(8) Brown, C. J.; Lain, S.; Verma, C. S.; Fersht, A. R.; Lane, D. P. Awakening Guardian Angels: Drugging the P53 Pathway. *Nat. Rev. Cancer* 2009, 9, 862-873.
(9) Krenning, L.; Feringa, F. M.; Shaltiel, I. A.; Van Den Berg, J.; Medema, R. H. Transient Activation of P53 in G2 Phase Is Sufficient to Induce Senescence. *Mol. Cell* 2014, 55, 59-72.
(10) Burgess, A.; Chia, K. M.; Haupt, S.; Thomas, D.; Haupt, Y.; Lim, E. Clinical Overview of MDM2/X-Targeted Therapies. *Front. Oncol.* 2016, 6,7.
(11) Haupt, Y.; Maya, R.; Kazaz, A.; Oren, M. Mdm2 Promotes the Rapid Degradation of P53. *Nature* 1997, 387, 296-299.
(12) Honda, R.; Tanaka, H.; Yasuda, H. Oncoprotein MDM2 Is a Ubiquitin Ligase E3 for Tumor Suppressor P53. *FEBS Lett.* 1997, 420, 25-27.
(13) Kubbutat, M. H. G.; Jones, S. N.; Vousden, K. H. Regulation of P53 Stability by Mdm2. *Nature* 1997, 387, 299-303.
(14) Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A, In Vivo Activation of the P53 Pathway by Small-Molecule Antagonists of MDM2. *Science* 2004, 303, 844-848.
(15) Harris, S. L.; Levine, A. J. The P53 Pathway: Positive and Negative Feedback Loops. *Oncogene* 2005, 24, 2899-2908.
(16) Ray-Coquard, I.; Blay, J.; Italiano, A.; Le Cesne, A.; Penel, N.; Zhi, J.; Heil, F.; Rueger, R.; Graves, B.; Ding, M.; Geho, D.; Middleton, S. A.; Vassilev, L. T.; Nichols, G. L.; Bid, B. N. Effect of the MDM2 Antagonist RG7112 on the P53 Pathway in Patients with MDM2-Amplified, Well-Differentiated or Dedifferentiated Liposarcoma: An Exploratory Proof-of-Mechanism Study. *Lancet Oncol.* 2012, 13, 1133-1140.
(17) Lerch, M. M.; Hansen, M. J.; van Dam, G. M.; Szymanski, Feringa, B. L. Emerging Targets in Photopharmacology. *Angew. Chem., Int. Ed.* 2016, 55, 10978-10999.
(18) Broichhagen, J.; Frank, J. A.; Trauner, D. A Roadmap to Success in Photopharmacology. *Acc. Chem. Res.* 2015, 48, 1947-1960.
(19) Velema, W. A.; van der Berg, J. P.; Szymanski, W.; Driessen, A. J. M.; Feringa, B. L. Orthogonal Control of Antibacterial Activity with Light. *ACS Chem. Biol.* 2014, 9, 1969-1974.
(20) Stanton-Humphreys, M. N.; Taylor, R. D. T.; McDougall, C.; Hart, M. L.; Brown, C. T. a; Emptage, N. J.; Conway, S. J. Wavelength-Orthogonal Photolysis of Neurotransmitters in Vitro. *Chem. Commun.* 2012, 48, 657-659.
(21) Gandioso, A.; Cano, M.; Massaguer, A.; Marchan, V. A Green Light-Triggerable RGD Peptide for Photocontrolled Targeted Drug Delivery: Synthesis and Photolysis Studies. *J. Org. Chem.* 2016, 81, 11556-11564.
(22) Klán, P.; Šolomek, T.; Bochet, C. G.; Blanc, A.; Givens, R.; Rubina, M.; Popik, V.; Kostikov, A.; Wirz, J. Photoremovable Protecting Groups in Chemistry and Biology: Reaction Mechanisms and Efficacy. *Chem. Rev.* 2013, 113, 119-191.
(23) Hansen, M. J.; Velema, W. A.; Lerch, M. M.; Szymanski, W.; Feringa, B. L. Wavelength-Selective Cleavage of Photoprotecting Groups: Strategies and Applications in Dynamic Systems. *Chem. Soc. Rev.* 2015, 44, 3358-3377.
(24) Weis, S.; Shafiq, Z.; Gropeanu, R. A.; del Campo, A. Ethyl Substituted Coumarin-4-Yl Derivatives as Photoremovable Protecting Groups for Amino Acids with Unproved Stability for SPPS. *J. Photochem. Photobiol. A Chem.* 2012, 241, 52-57.
(25) Gandioso, A.; Contreras, S.; Melnyk, I.; Oliva, J.; Nonell, S.; Velasco, D.; García-Amorós, J.; Marchán, V. Development of Green/Red-Absorbing Chromophores Based on a Coumarin Scaffold That Are Useful as Caging Groups. *J. Org. Chem.* 2017, 82, 5398-5408.
(26) Shu, L.; Gu, C.; Fishlock, D.; Li, Z. Practical Synthesis of MDM2 Antagonist RG7388. Part 1; A Cu(II)-Catalyzed Asymmetric [3+2] Cycloaddition. *Org. Process Res. Dev.* 2016, 20, 2050-2056.
(27) Rimmler, G.; Alker, A.; Bosco, M.; Diodone, R.; Fishlock, D.; Hildbrand, S.; Kuhn, B.; Moessner, C.; Peters, C.; Rege, P. D.; Schantz, M. Practical Synthesis of MDM2 Antagonist RG7388, Part 2: Development of the Cu(I) Catalyzed [3+2] Asymmetric Cycloaddition Process for the Manufacture of Idasanutlin. *Org. Process Res. Dev.* 2016, 20, 2057-2066.
(28) Tsakos, M.; Schaffert, E. S.; Clement, L. L.; Villadsen, N. L.; Poulsen, T. B. Ester Coupling Reactions—an Enduring Challenge in the Chemical Synthesis of Bioactive Natural Products. *Nat. Prod. Rep.* 2015, 32, 605-632.
(29) Ding, Q.; Zhang, Z.; Liu, J.-J.; Jiang, N.; Zhang, J.; Ross, T. M.; Chu, X.-J.; Bartkovitz, D.; Podlaski, F.; Janson, C.; Tovar, C.; Filipovic, Z. M.; Higgins, B.; Glenn, K.; Packman, K.; Vassilev, L. T.; Graves, B. Discovery of RG7388, a Potent and Selective P53-MDM2 Inhibitor in Clinical Development. *J. Med. Chem.* 2013, 56, 5979-5983.

The invention claimed is:
1. A compound having the chemical structure

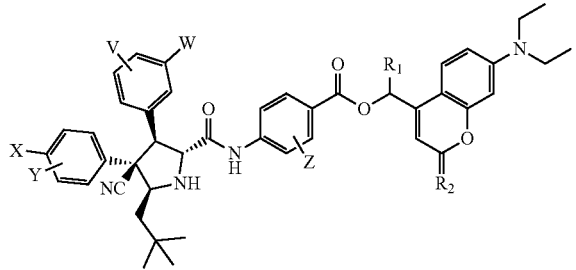

wherein
V is —H or —F;
W is —F, —Cl or —Br;
X is selected from the group consisting of H, F, Cl, Br, I, cyano, nitro, ethynyl, cyclopropyl, methyl, ethyl, isopropyl, vinyl and methoxy;
Y is independently selected from the group consisting of —H, —F, —Cl, —Br, —I, —CN, —OH, nitro, lower alkyl, cycloalkyl, lower alkoxy, lower alkenyl, cycloalkenyl and lower alkynyl;
Z is Cl, F, Br, I or lower alkoxy;
$R_1$ is —H or —$CH_3$
$R_2$ is O, S or $C(CN)_2$
or a pharmaceutically acceptable salt thereof.
2. The compound according to claim 1, wherein X is selected from the group consisting of F, Cl, Br and I.
3. The compound according to claim 1, wherein Y is selected from —H, —F and —Cl.
4. The compound according to claim 1, wherein Z is Cl or —$OCH_3$.

5. The compound according to claim 1, wherein W is —Cl, and/or wherein V is —F.

6. The compound according to claim 1, wherein $R_1$ is —CH.

7. The compound according to claim 1, wherein $R_2$ is O.

8. A compound of the formula

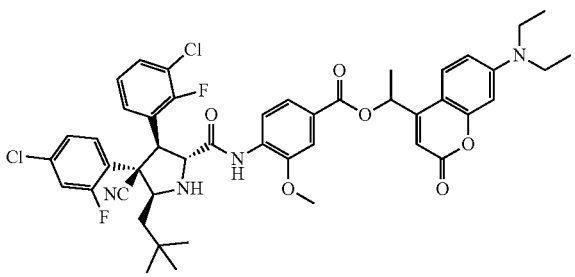 [SMILES: CCN(CC)c1ccc2c(C(C)OC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)cc(=O)oc2c1]

or a pharmaceutically acceptable salt thereof.

9. A pharmaceutical composition comprising a compound according to claim 1 and a pharmaceutically acceptable carrier, vehicle or diluent.

10. The compound according to claim 1 for use as a photo-activatable inhibitor of the interaction between MDM2 and p53.

11. The compound according to claim 1 for use in a method of treating in a subject a disorder mediated by a p53-MDM2 interaction.

12. The compound for use according to claim 11, wherein said disorder is cancer.

13. The compound for use according to claim 11, wherein said method comprises administering said compound to a subject in need thereof, followed by selectively illuminating with light, at a predetermined time and/or location of the body of said subject, thereby converting said compound into a biologically active agent.

14. The compound for use according to claim 13, comprising the use of an optical probe to illuminate a location within the body of said subject.

15. The compound for use according to claim 10, wherein said compound is of the formula

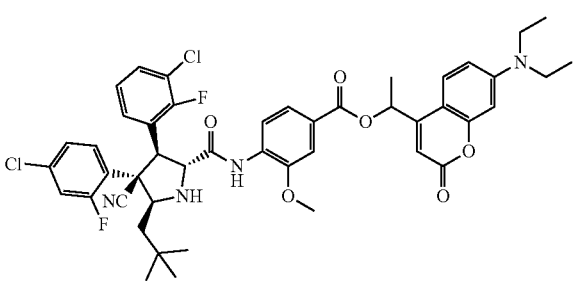 [SMILES: CCN(CC)c1ccc2c(C(C)OC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)cc(=O)oc2c1]

or a pharmaceutically acceptable salt thereof.

16. A method for treating a disorder mediated by a p53-MDM2 interaction in a subject, comprising administering to the subject a therapeutically effective amount of a compound according to claim 1.

17. The method according to claim 16, wherein said disorder is cancer.

18. The method according to claim 16, wherein said method comprises administering said compound to a subject in need thereof, followed by selectively illuminating with light, at a predetermined time and/or location of the body of said subject, thereby converting said compound into a biologically active agent.

19. The method according to claim 18, comprising the use of an optical probe to illuminate a location within the body of said subject.

20. The method according to claim 16, wherein said compound is of the formula

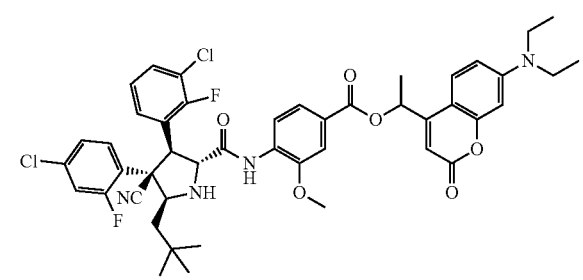

or a pharmaceutically acceptable salt thereof.

21. The compound according to claim 2, wherein X is —Cl or —F.

22. The compound for use according to claim 12, wherein said disorder is a solid tumor.

23. The compound for use according to claim 22, wherein the solid tumor is a breast, colon, lung or prostate tumor.

24. The compound for use according to claim 13, wherein the light is X >400 nm.

25. The method according to claim 17, wherein said disorder is a solid tumor.

26. The method according to claim 25, wherein the solid tumor is a breast, colon, lung or prostate tumor.

27. The compound for use according to claim 18, wherein the light is $\lambda \geq 400$ nm.

* * * * *